United States Patent
Fujiwara et al.

(10) Patent No.: US 9,458,144 B2
(45) Date of Patent: Oct. 4, 2016

(54) MONOMER, POLYMER, RESIST COMPOSITION, AND PATTERNING PROCESS

(71) Applicant: Shin-Etsu Chemical Co., Ltd., Tokyo (JP)

(72) Inventors: Takayuki Fujiwara, Joetsu (JP); Masayoshi Sagehashi, Joetsu (JP); Koji Hasegawa, Joetsu (JP); Ryosuke Taniguchi, Joetsu (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 0 days.

(21) Appl. No.: 14/689,392

(22) Filed: Apr. 17, 2015

(65) Prior Publication Data

US 2015/0322027 A1    Nov. 12, 2015

(30) Foreign Application Priority Data

May 9, 2014    (JP) ................. 2014-097364

(51) Int. Cl.
| | | |
|---|---|---|
| *C07D 307/92* | (2006.01) | |
| *C07D 307/20* | (2006.01) | |
| *C07D 307/32* | (2006.01) | |
| *C07D 307/33* | (2006.01) | |
| *C07D 493/10* | (2006.01) | |
| *C07D 407/12* | (2006.01) | |
| *C07D 307/94* | (2006.01) | |

(52) U.S. Cl.
CPC ........... *C07D 407/12* (2013.01); *C07D 307/20* (2013.01); *C07D 307/32* (2013.01); *C07D 307/33* (2013.01); *C07D 307/94* (2013.01); *C07D 493/10* (2013.01)

(58) Field of Classification Search
CPC  C07D 307/20; C07D 307/32; C07D 307/33; C07D 307/94; C07D 493/10; C07D 407/12
See application file for complete search history.

(56) References Cited

U.S. PATENT DOCUMENTS

| | | | |
|---|---|---|---|
| 6,787,283 B1 | 9/2004 | Aoai et al. | |
| 7,531,289 B2 * | 5/2009 | Kinsho ................ | C07D 307/20 430/270.1 |
| 8,017,304 B2 | 9/2011 | Tarutani et al. | |
| 8,034,547 B2 | 10/2011 | Tsubaki et al. | |
| 8,241,840 B2 | 8/2012 | Tsubaki et al. | |
| 8,603,733 B2 | 12/2013 | Tarutani et al. | |

FOREIGN PATENT DOCUMENTS

| | | |
|---|---|---|
| JP | 2001-033971 A | 2/2001 |
| JP | 2008-281974 A | 11/2008 |
| JP | 2008-281975 A | 11/2008 |
| JP | 2008-281980 A | 11/2008 |
| JP | 2009-025707 A | 2/2009 |
| JP | 2009-025723 A | 2/2009 |
| JP | 2009-053657 A | 3/2009 |
| JP | 4631297 B2 | 2/2011 |
| JP | 2011-197339 A | 10/2011 |
| WO | 20131183380 A1 | 12/2013 |

* cited by examiner

*Primary Examiner* — Sun Jae Yoo
(74) *Attorney, Agent, or Firm* — Westerman, Hattori, Daniels & Adrian, LLP

(57) ABSTRACT

A monomer (1) is prepared by reacting a compound (9) with a base or metal to form a metal enolate reagent, and reacting the metal enolate reagent with an acyloxyketone compound (8). A polymer derived from the monomer is used as base resin to formulate a resist composition, which is shelf stable and displays a high dissolution contrast, controlled acid diffusion and low roughness in forming positive pattern via alkaline development and in forming negative pattern via organic solvent development.

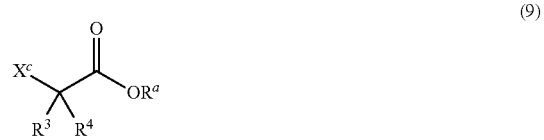

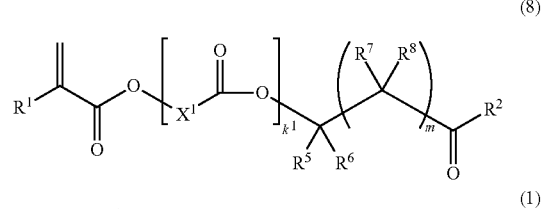

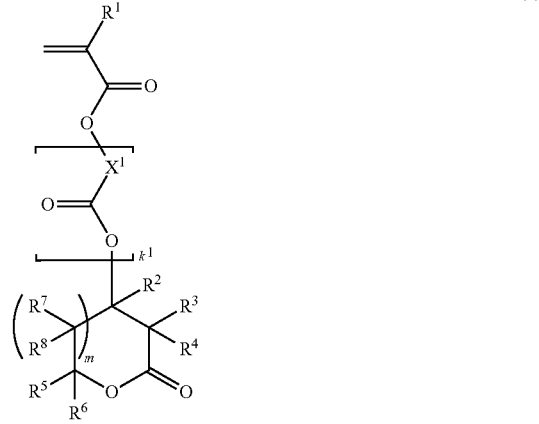

4 Claims, No Drawings

MONOMER, POLYMER, RESIST COMPOSITION, AND PATTERNING PROCESS

CROSS-REFERENCE TO RELATED APPLICATION

This non-provisional application claims priority under 35 U.S.C. §119(a) on Patent Application No. 2014-097364 filed in Japan on May 9, 2014, the entire contents of which are hereby incorporated by reference.

TECHNICAL FIELD

This invention relates to a method for preparing a monomer useful as a starting reactant for functional, pharmaceutical and agricultural chemicals. The monomer is useful for the preparation of a polymer which is used as a base resin to formulate a radiation-sensitive resist composition having high transparency to radiation of wavelength 500 nm or less, especially 300 nm or less, typically KrF, ArF or $F_2$ laser radiation, and improved development properties.

BACKGROUND ART

To meet the demand for higher integration density and operating speed of LSIs, the effort to reduce the pattern rule is in rapid progress. The wide-spreading flash memory market and the demand for increased storage capacities drive forward the miniaturization technology. As the advanced miniaturization technology, manufacturing of microelectronic devices at the 65-nm node by the ArF lithography has been implemented in a mass scale. Manufacturing of 45-nm node devices by the next generation ArF immersion lithography is approaching to the verge of high-volume application. The candidates for the next generation 32-nm node include ultra-high NA lens immersion lithography using a liquid having a higher refractive index than water in combination with a high refractive index lens and a high refractive index resist film, extreme ultraviolet (EUV) lithography of 13.5 nm wavelength, and double patterning version of the ArF lithography, on which active research efforts have been made.

Besides the positive tone resist by alkaline development, a highlight is recently put on the negative tone resist by organic solvent development. It would be desirable if a very fine hole pattern, which is not achievable with the positive tone, is resolvable through negative tone exposure. To this end, a positive resist composition featuring a high resolution is subjected to organic solvent development to form a negative pattern. An attempt to double a resolution by combining two developments, alkaline development and organic solvent development is under study.

As the ArF resist composition for negative tone development with organic solvent, positive ArF resist compositions of the prior art design may be used. Such pattern forming processes are described in Patent Documents 1 to 6.

These patent documents disclose resist materials for organic solvent development comprising a copolymer of hydroxyadamantane methacrylate, a copolymer of norbornane lactone methacrylate, a copolymer of methacrylate having acidic groups including carboxyl, sulfo, phenol, thiol and other groups substituted with two or more acid labile groups, and a copolymer of methacrylate having a cyclic acid-stable group ester, and pattern forming processes using the same.

The ester unit having a carboxyl group protected with an acid labile group is one of predominant constituent units of base resins in currently available chemically amplified resist compositions. Patent Document 7 discloses a positive resist comprising units of hydroxyadamantane methacrylate having a hydroxyl group protected with a tertiary alkyl group. Also, Patent Document 8 discloses formation of a negative pattern via organic solvent development, using a base resin comprising those units having a hydroxyl group protected in acetal or tertiary ether form as the sole acid labile unit.

Polymerization units having such an acid labile group are important as constituent units of the base resin in the current chemically amplified resist compositions. In addition, polymerization units having an adhesive group are also important for forming patterns at high resolution when considered from the standpoints of dissolution contrast and acid diffusion control. These polymerization units include methacrylic compounds having lactone units of butyrolactone, valerolactone, norbornanelactone or cyclohexanelactone skeleton, and sultone units. Among others, adhesive units having butyrolactone skeleton which is a 5-membered lactone are mainly used, with a focus placed on α-methacryloyloxy-γ-butyrolactone and β-methacryloyloxy-γ-butyrolactone skeletons.

Patent Documents 9 and 10 disclose methods for the preparation of β-methacryloyloxy-γ-butyrolactone compounds having a substituent on lactone ring, and their use as resist material.

CITATION LIST

Patent Document 1: JP-A 2008-281974
Patent Document 2: JP-A 2008-281975
Patent Document 3: JP-A 2008-281980
Patent Document 4: JP-A 2009-053657
Patent Document 5: JP-A 2009-025707
Patent Document 6: JP-A 2009-025723
Patent Document 7: JP 4631297
Patent Document 8: JP-A 2011-197339
Patent Document 9: WO 2013/183380
Patent Document 10: JP-A 2001-033971

DISCLOSURE OF INVENTION

The above-mentioned β-(meth)acryloyloxy-γ-butyrolactone compounds are widely used as the constituent unit of a resist base resin. Many problems including stability of compounds, careful handling of starting reactants, difficulty of treatment, expense, and special reactor setup must be solved before the compounds can be produced on an industrial scale. There is a need for an industrial method of preparing β-(meth)acryloyloxy-γ-butyrolactone compounds in a stable manner and large scale.

An object of the invention is to provide a method for preparing a monomer which is useful to constitute an adhesive unit of a base resin so that a photoresist composition comprising the base resin may display improved performance properties such as dissolution contrast, controlled acid diffusion and low roughness in both alkaline development and organic solvent development.

The inventors have found that when reaction involving rearrangement of (meth)acryloyloxy group is utilized, β-(meth)acryloyloxy-γ-butyrolactone compounds and β-(meth)acryloyloxy-γ-valerolactone compounds can be prepared via a few steps in high yields without forming an intermediate in the form of β-hydroxylactone or β-halolactone and without a need for a special reactor.

Further, when a polymer derived from the monomer is used as adhesive unit of a base resin in a resist composition, the resist composition is effective not only in forming positive patterns by conventional alkaline development, but also in image formation via positive/negative reversal by organic solvent development, offering improved performance properties such as pattern collapse resistance, high dissolution contrast, acid diffusion control, and low roughness.

In one aspect, the invention provides a method for preparing a monomer having the general formula (1), comprising the steps of reacting a compound having the general formula (9) with a base or a metal selected from Group 1A, 2A and 2B metals to form a metal enolate reagent, and reacting the metal enolate reagent with an acyloxyketone compound having the general formula (8).

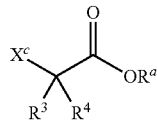

(9)

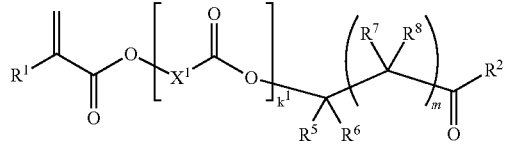

(8)

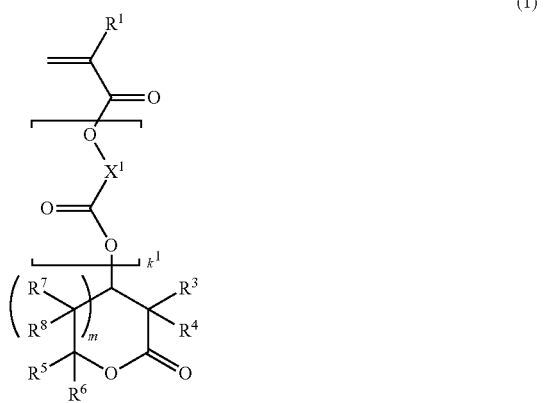

(1)

Herein $R^1$ is hydrogen, methyl or trifluoromethyl; $R^2$ is hydrogen or a straight, branched or cyclic $C_1$-$C_{10}$ monovalent hydrocarbon group which may contain a heteroatom; $R^3$ and $R^4$ are each independently hydrogen or a straight, branched or cyclic $C_1$-$C_{10}$ monovalent hydrocarbon group which may contain a heteroatom, $R^3$ and $R^4$ may bond together to form a ring with the carbon atom to which they are attached; $R^5$ and $R^6$ are each independently hydrogen or a straight, branched or cyclic $C_1$-$C_{10}$ monovalent hydrocarbon group which may contain a heteroatom, $R^5$ and $R^6$ may bond together to form a ring with the carbon atom to which they are attached; $R^7$ and $R^8$ are each independently hydrogen or a straight, branched or cyclic $C_1$-$C_{10}$ monovalent hydrocarbon group which may contain a heteroatom, $R^7$ and $R^8$ may bond together to form a ring with the carbon atom to which they are attached; $X^1$ is a $C_1$-$C_{10}$ alkylene group which may have an ether, ester, lactone ring or hydroxyl, or a $C_6$-$C_{10}$ arylene group; m is 0 or 1; in case of m=0, $R^2$ may bond with $R^5$ or $R^6$ to form a ring with the carbon atoms to which they are attached; in case of m=1, $R^2$ may bond with $R^7$ or $R^8$ to form a ring with the carbon atoms to which they are attached; $k^1$ is 0 or 1; $X^c$ is hydrogen or halogen; and $R^a$ is a straight or branched $C_1$-$C_{10}$ monovalent hydrocarbon group.

In another aspect, the invention provides a method for preparing a monomer having the general formula (1), comprising the steps of reacting a compound having the general formula (9) with a base or a metal selected from Group 1A, 2A and 2B metals to form a metal enolate reagent, reacting the metal enolate reagent with an acyloxyketone compound having the general formula (8), isolating the resulting intermediate having the general formula (12), and lactonizing the intermediate.

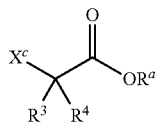

(9)

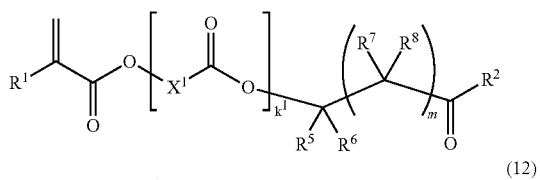

(8)

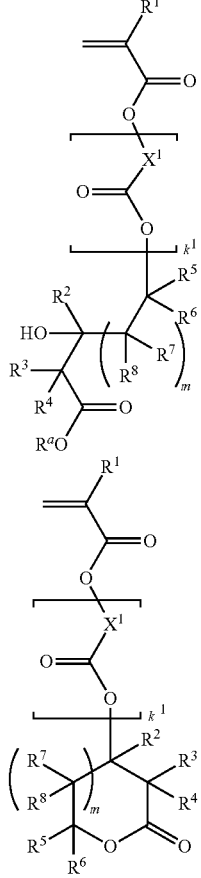

(12)

Herein $R^1$ to $R^8$, $X^1$, m, k, $X^c$, and $R^a$ are as defined above.

Preferably, the acyloxyketone compound having formula (8) is prepared by reaction of a haloketone compound having the general formula (4) with a carboxylic acid salt compound having the general formula (5).

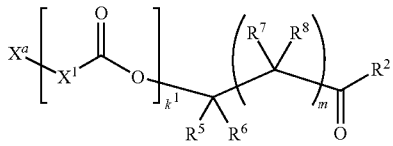

(4)

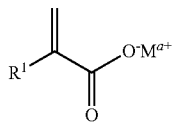

(5)

Herein $R^1$, $R^2$, $R^5$, $R^6$, $R^7$, $R^8$, $X^1$, m and $k^1$ are as defined above, $X^a$ is halogen, and $M^a$ is Li, Na, K, $Mg_{1/2}$, $Ca_{1/2}$ or substituted or unsubstituted ammonium.

Also preferably, the acyloxyketone compound having formula (8) is prepared by reaction of an alcohol compound having the general formula (6) with an esterifying agent having the general formula (7).

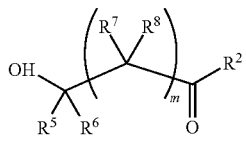

(6)

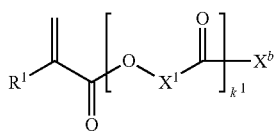

(7)

Herein $R^1$, $R^2$, $R^5$, $R^6$, $R^7$, $R^8$, $X^1$, m and $k^1$ are as defined above, $X^b$ is halogen, hydroxyl or —$OR^b$, and $R^b$ is methyl, ethyl or a group having the formula (11):

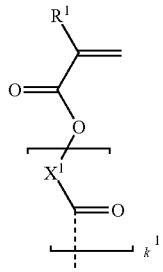

(11)

wherein $R^1$, $X^1$ and $k^1$ are as defined above, and the broken line denotes a valence bond.

Advantageous Effects of Invention

The inventive monomer is useful as a starting reactant for functional, pharmaceutical and agricultural chemicals. The monomer is particularly useful for the preparation of a polymer which is used as a base resin to formulate a radiation-sensitive resist composition having high transparency to radiation of wavelength 500 nm or less, especially 300 nm or less, and improved development properties. When a polymer derived from the inventive monomer is used as base resin in a resist composition, the resulting resist composition is improved in resist properties such as pattern collapse resistance, high dissolution contrast, acid diffusion control, and low roughness in either of positive tone pattern formation by conventional alkaline development and image formation via positive/negative reversal by organic solvent development.

DESCRIPTION OF EMBODIMENTS

In the disclosure, the singular forms "a," "an" and "the" include plural referents unless the context clearly dictates otherwise. The notation (Cn-Cm) means a group containing from n to m carbon atoms per group. In the chemical formulae, the broken line denotes a valence bond.

The abbreviations and acronyms have the following meaning.

EUV: extreme ultraviolet
PAG: photoacid generator
Mw: weight average molecular weight
Mn: number average molecular weight
Mw/Mn: molecular weight distribution or dispersity
GPC: gel permeation chromatography
PEB: post-exposure bake
LWR: line width roughness It is understood that for some structures represented by chemical formulae, there can exist enantiomers and diastereomers because of the presence of asymmetric carbon atoms. In such a case, a single formula collectively represents all such isomers. The isomers may be used alone or in admixture.

First, the monomer to be prepared by the inventive method is described. The monomer has the general formula (1).

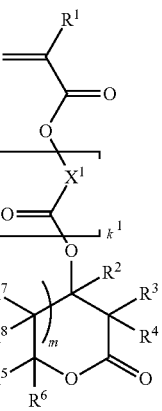

(1)

Herein $R^1$ is hydrogen, methyl or trifluoromethyl. $R^2$ is hydrogen or a straight, branched or cyclic $C_1$-$C_{10}$ monovalent hydrocarbon group which may contain a heteroatom. $R^3$ and $R^4$ are each independently hydrogen or a straight, branched or cyclic $C_1$-$C_{10}$ monovalent hydrocarbon group which may contain a heteroatom, $R^3$ and $R^4$ may bond together to form a ring with the carbon atom to which they are attached. $R^5$ and $R^6$ are each independently hydrogen or a straight, branched or cyclic $C_1$-$C_{10}$ monovalent hydrocarbon group which may contain a heteroatom, $R^5$ and $R^6$ may bond together to form a ring with the carbon atom to which they are attached. $R^7$ and $R^8$ are each independently hydrogen or a straight, branched or cyclic $C_1$-$C_{10}$ monovalent hydrocarbon group which may contain a heteroatom, $R^7$ and $R^8$ may bond together to form a ring with the carbon atom to which they are attached. $X^1$ is a $C_1$-$C_{10}$ alkylene group which may have an ether moiety, ester moiety, lactone ring or hydroxyl moiety, or a $C_6$-$C_{10}$ arylene group. The subscript m is 0 or 1. In case of m=0, $R^2$ may bond with $R^5$ or $R^6$ to form a ring with the carbon atoms to which they are attached. In case of m=1, $R^2$ may bond with $R^7$ or $R^8$ to form a ring with the carbon atoms to which they are attached. The subscript $k^1$ is 0 or 1.

In formula (1), typical examples of the straight, branched or cyclic $C_1$-$C_{10}$ monovalent hydrocarbon group represented by $R^2$ to $R^8$ include straight, branched or cyclic alkyl groups such as methyl, ethyl, propyl, isopropyl, n-butyl, sec-butyl, tert-butyl, cyclopentyl, cyclohexyl, 2-ethylhexyl, n-octyl, norbornyl, tricyclodecanyl, and adamantyl; alkenyl and alkynyl groups such as vinyl, allyl, ethynyl and propargyl; aryl groups such as phenyl and naphthyl; and aralkyl groups such as benzyl. When the monovalent hydrocarbon group contains a heteroatom, suitable heteroatoms include nitrogen, oxygen and sulfur. Examples of the monovalent hydrocarbon group containing a heteroatom are shown below.

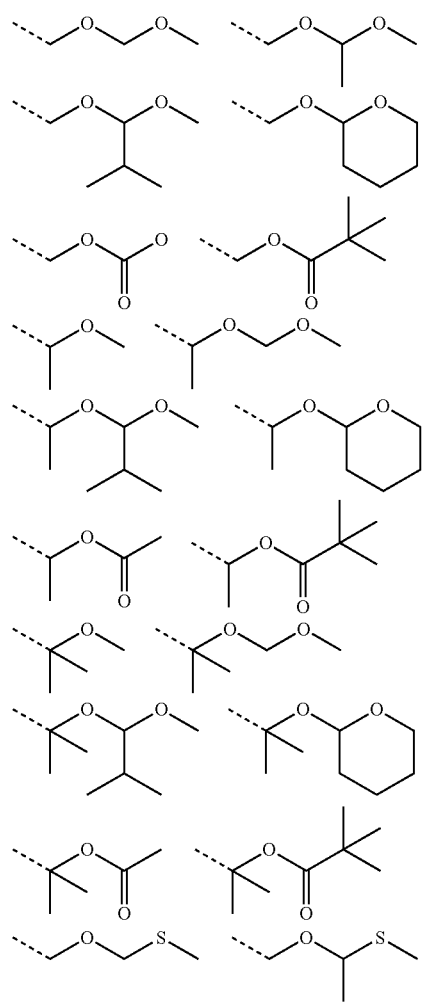

-continued

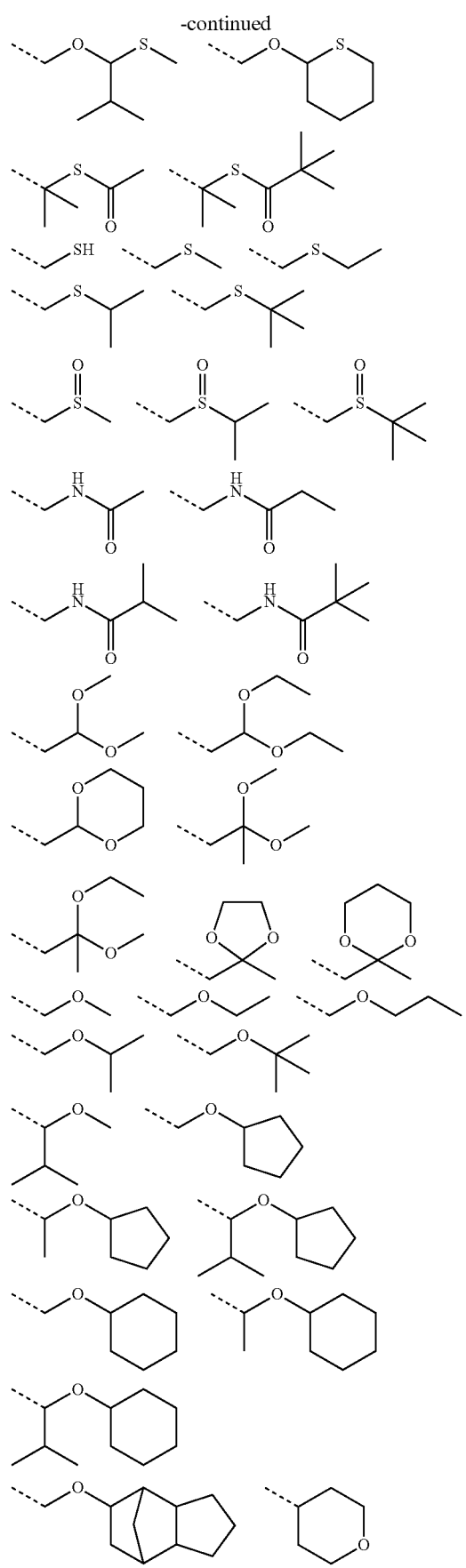

-continued

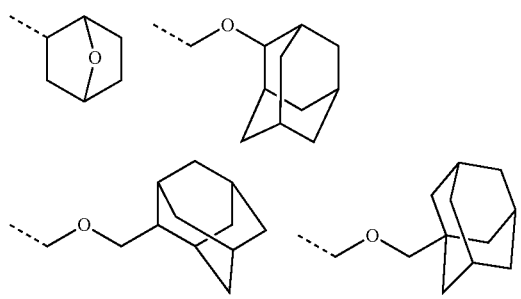

When a pair of $R^3$ and $R^4$, $R^5$ and $R^6$, or $R^7$ and $R^8$ bond together to form a ring, examples of the ring are shown below.

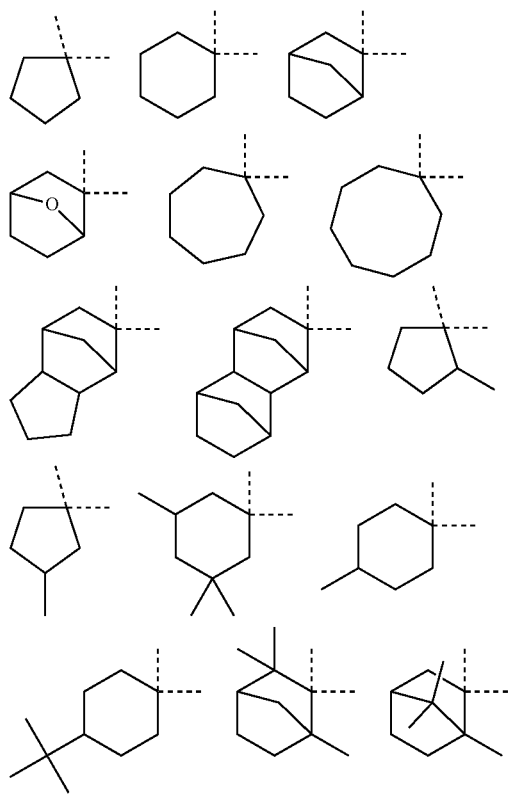

In formula (1), $X^1$ is a $C_1$-$C_{10}$ alkylene group which may have an ether moiety, ester moiety, lactone ring or hydroxyl moiety, or a $C_6$-$C_{10}$ arylene group, examples of which are shown below.

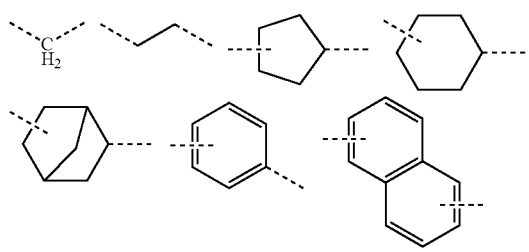

-continued

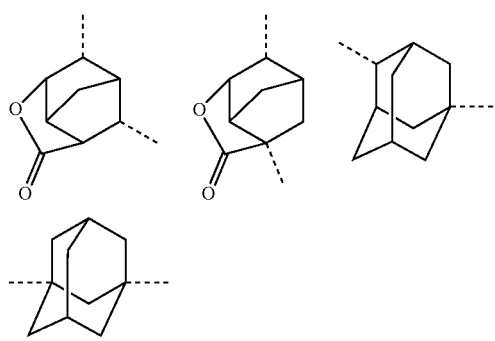

Illustrative, non-limiting examples of the monomer having formula (1) are shown below.

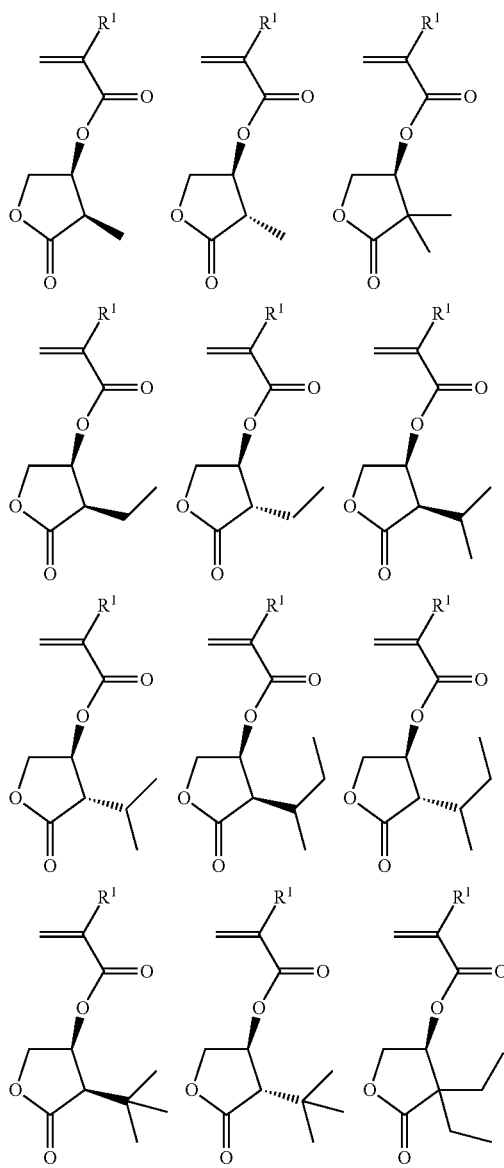

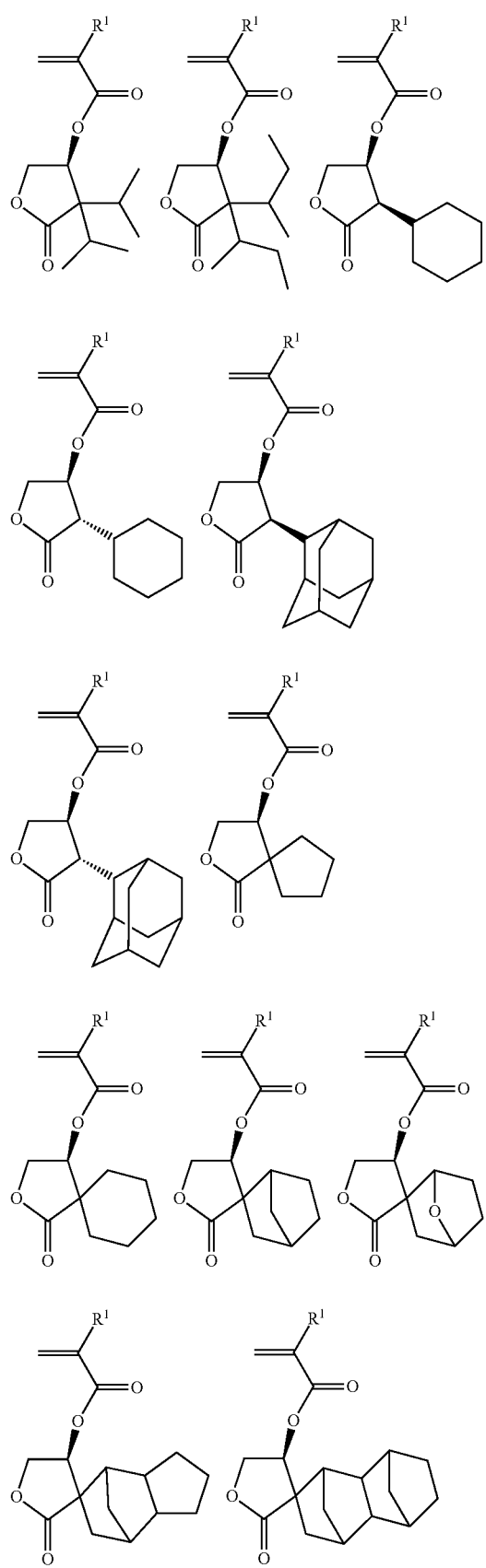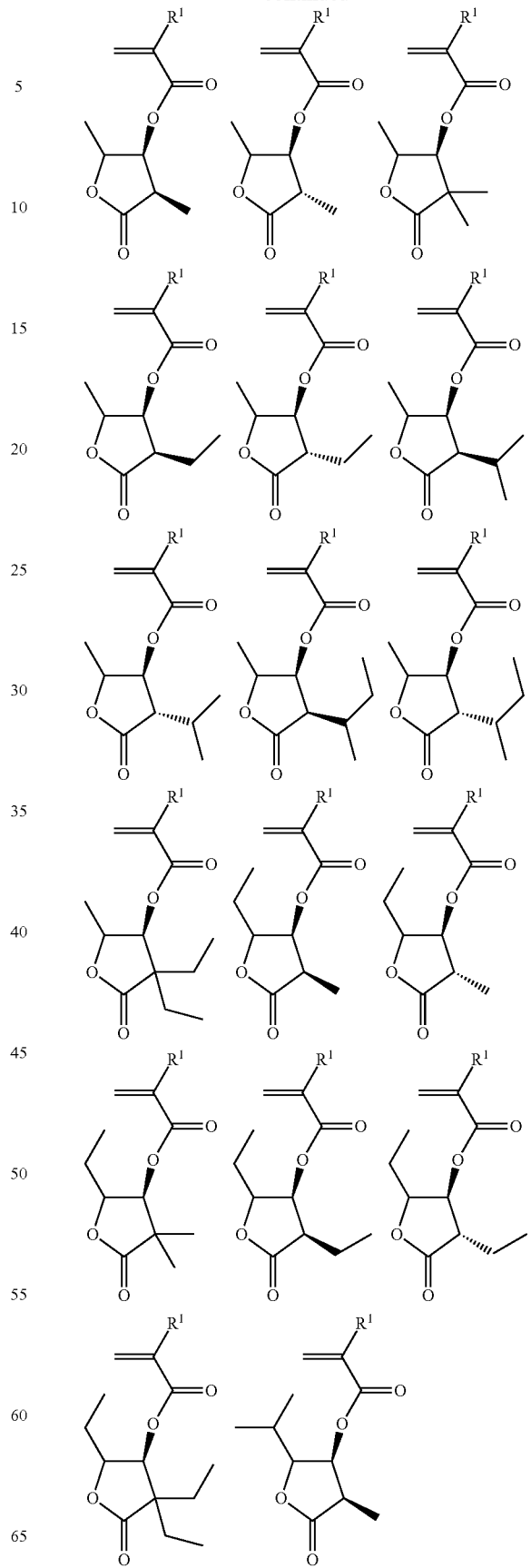

-continued
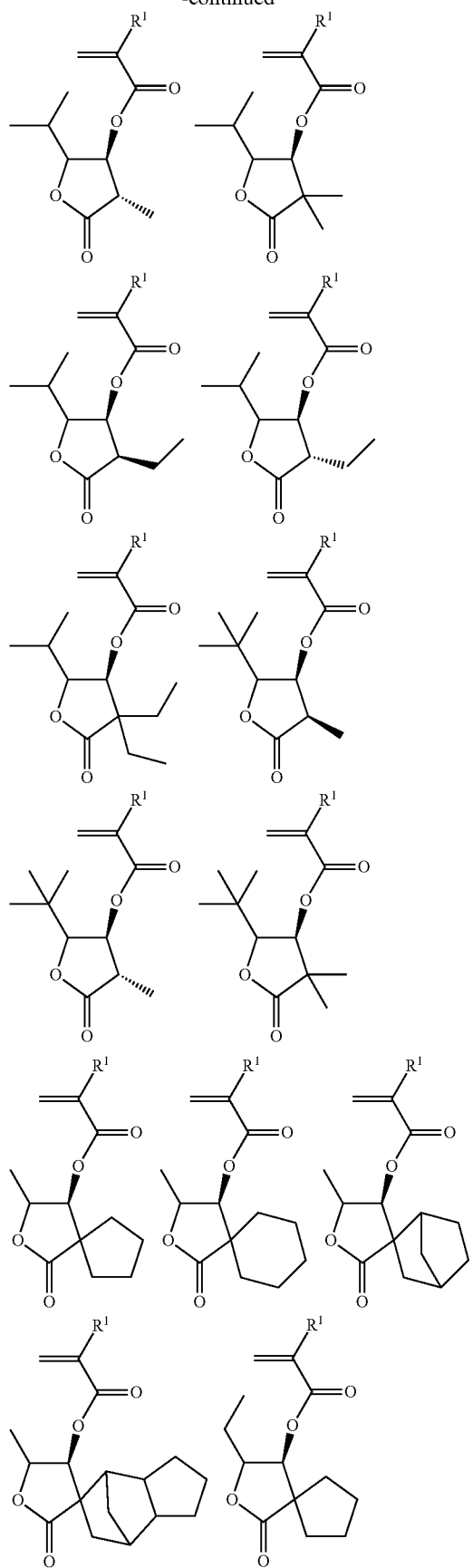
-continued
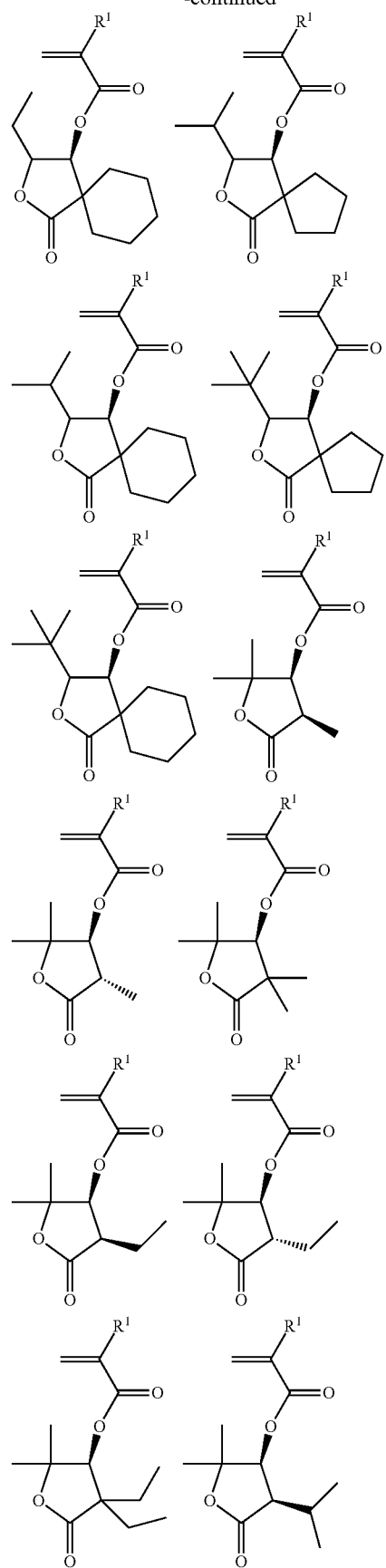

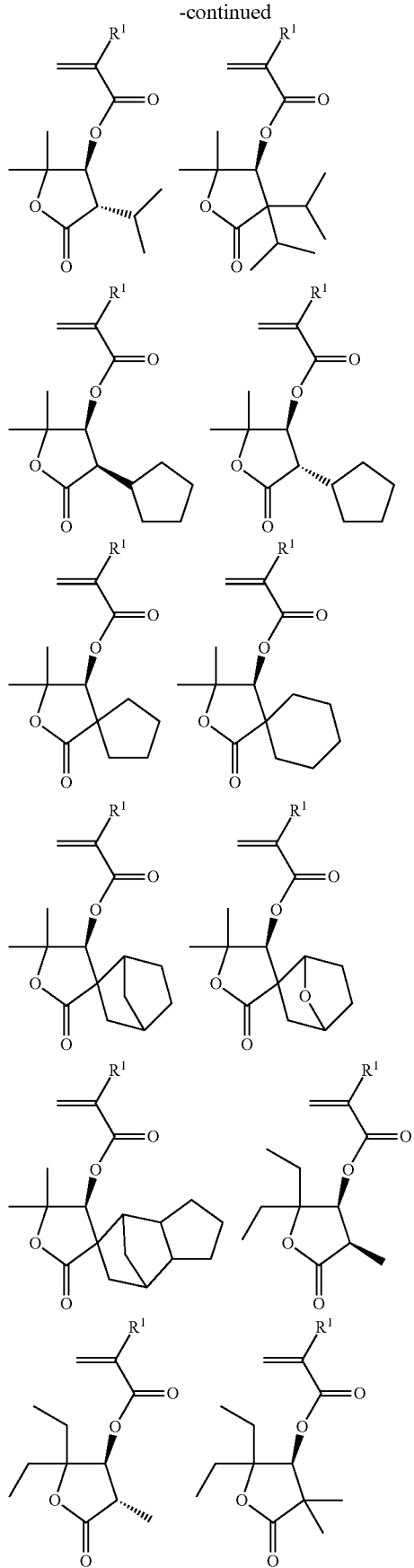
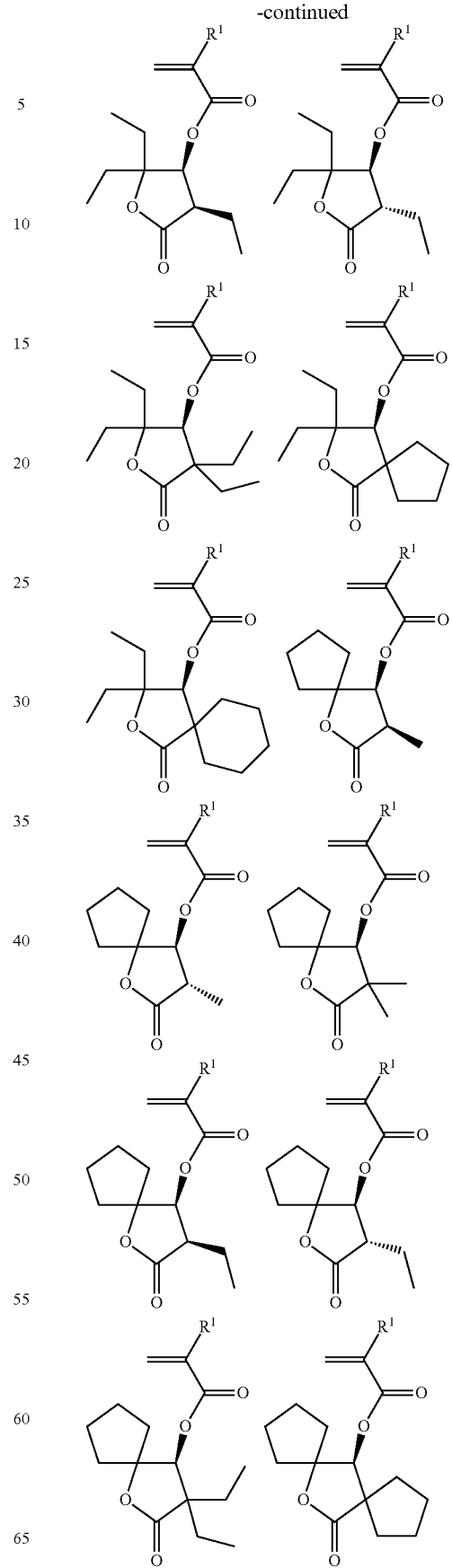

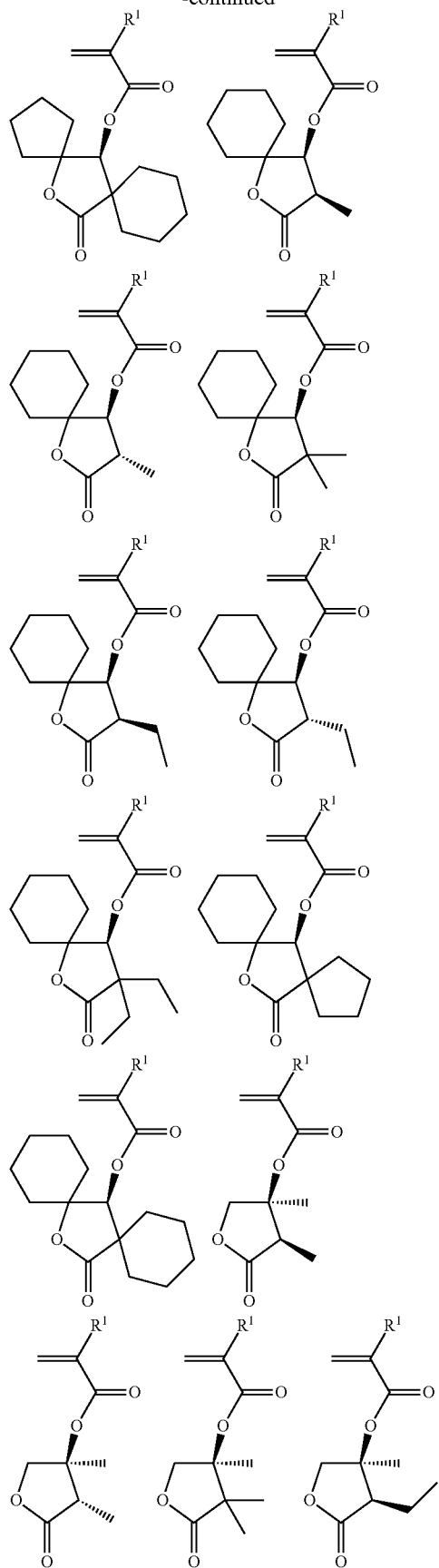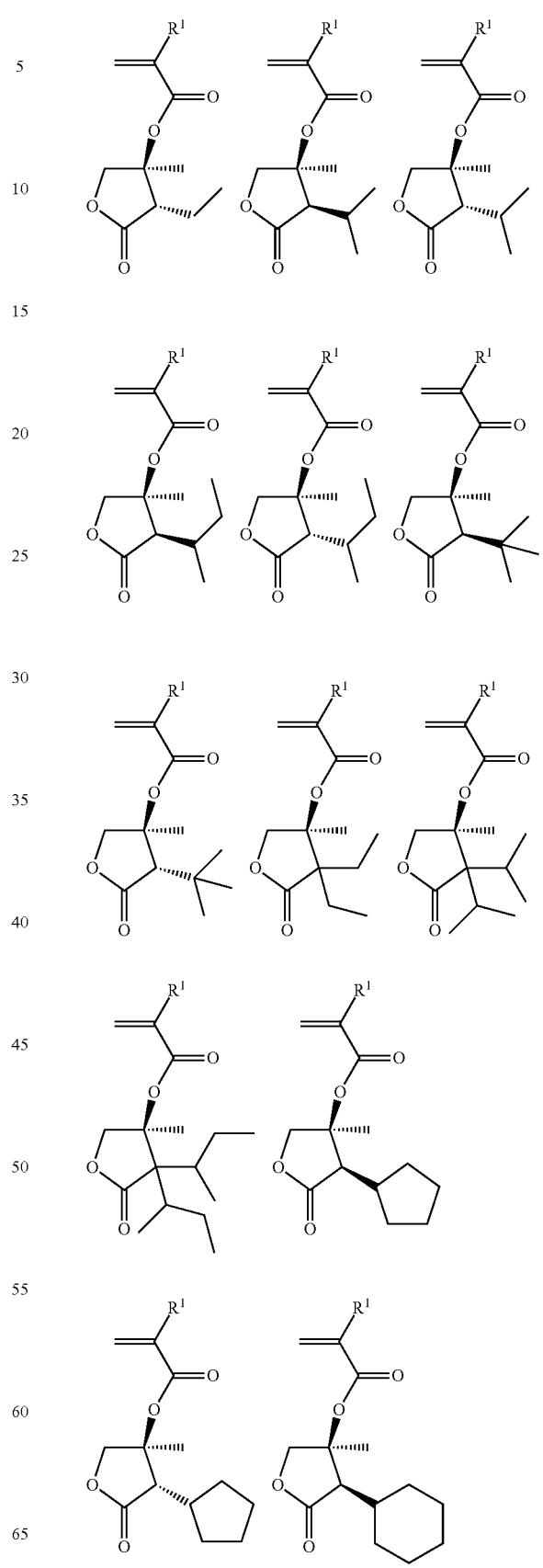

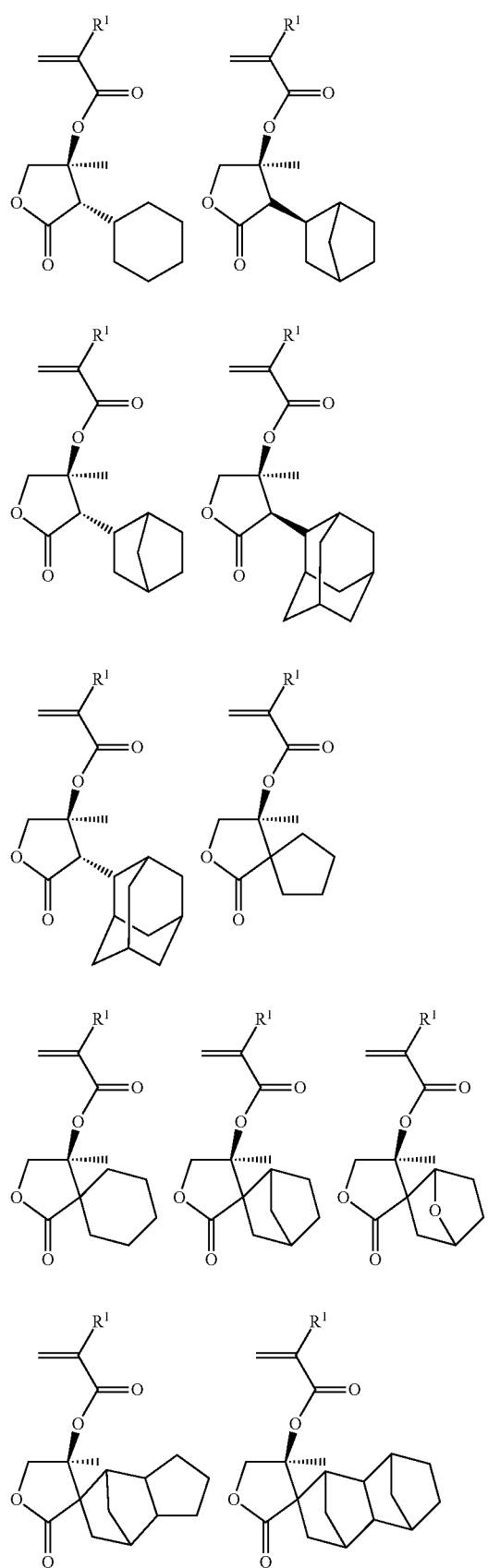
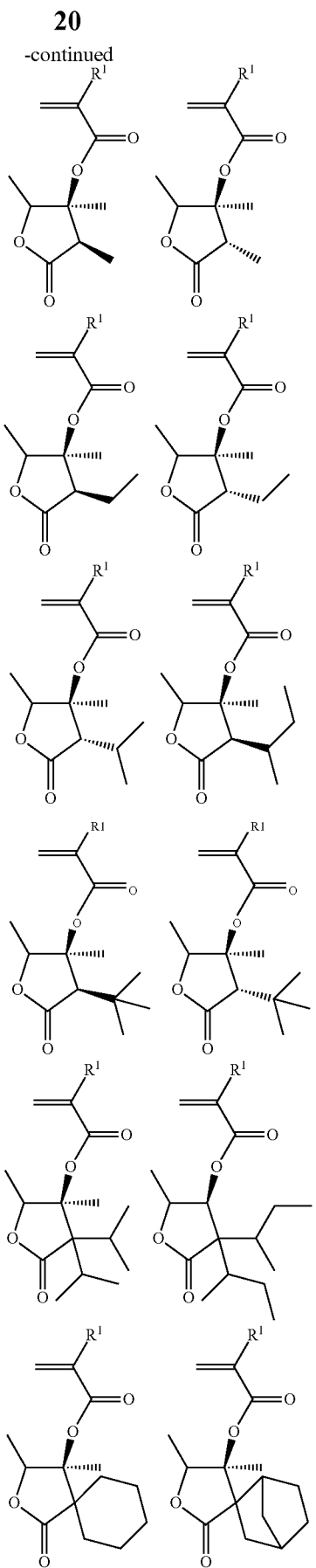

-continued
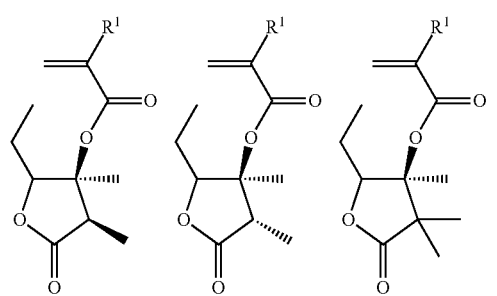
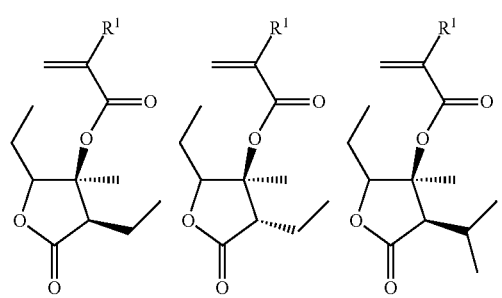
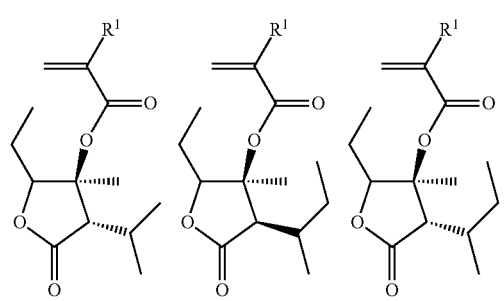
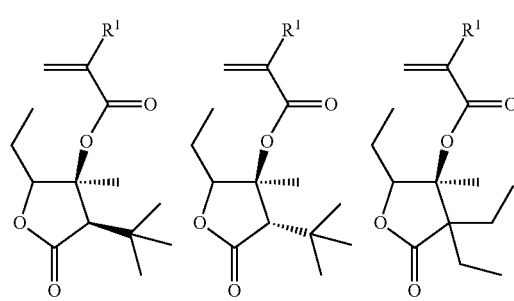
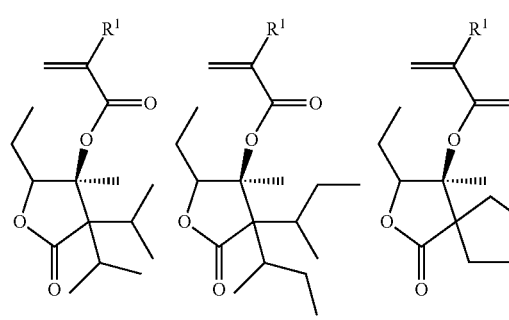
-continued
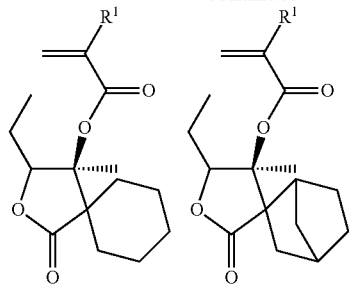
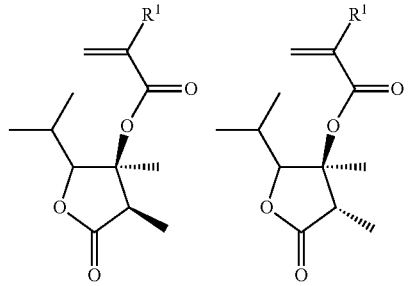
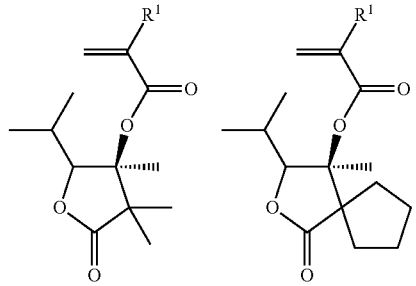
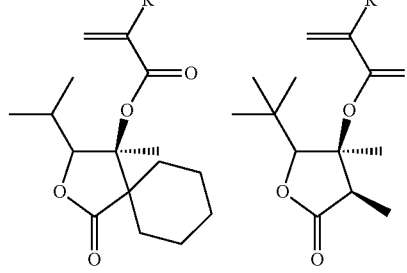
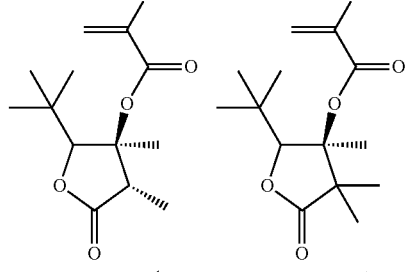
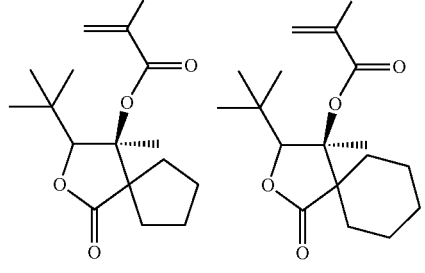

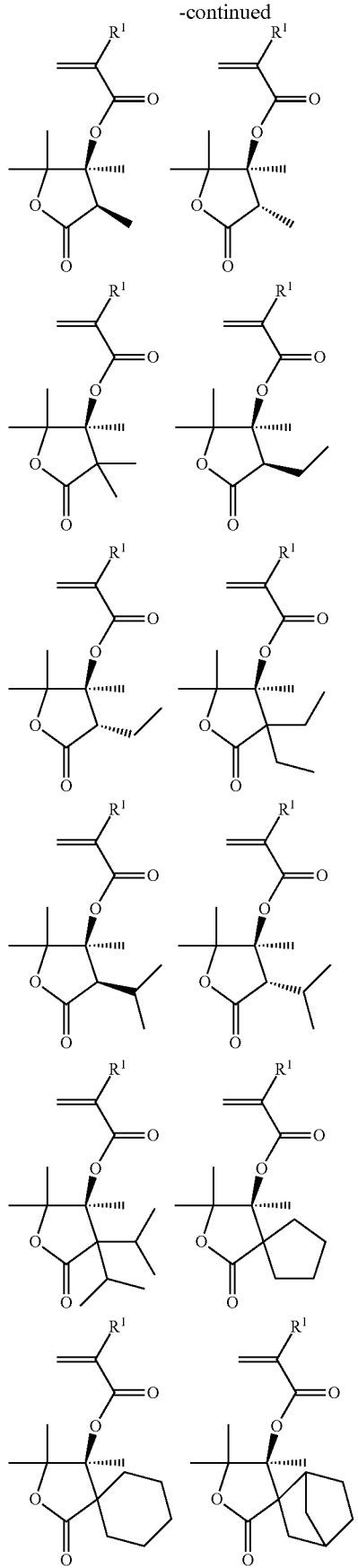
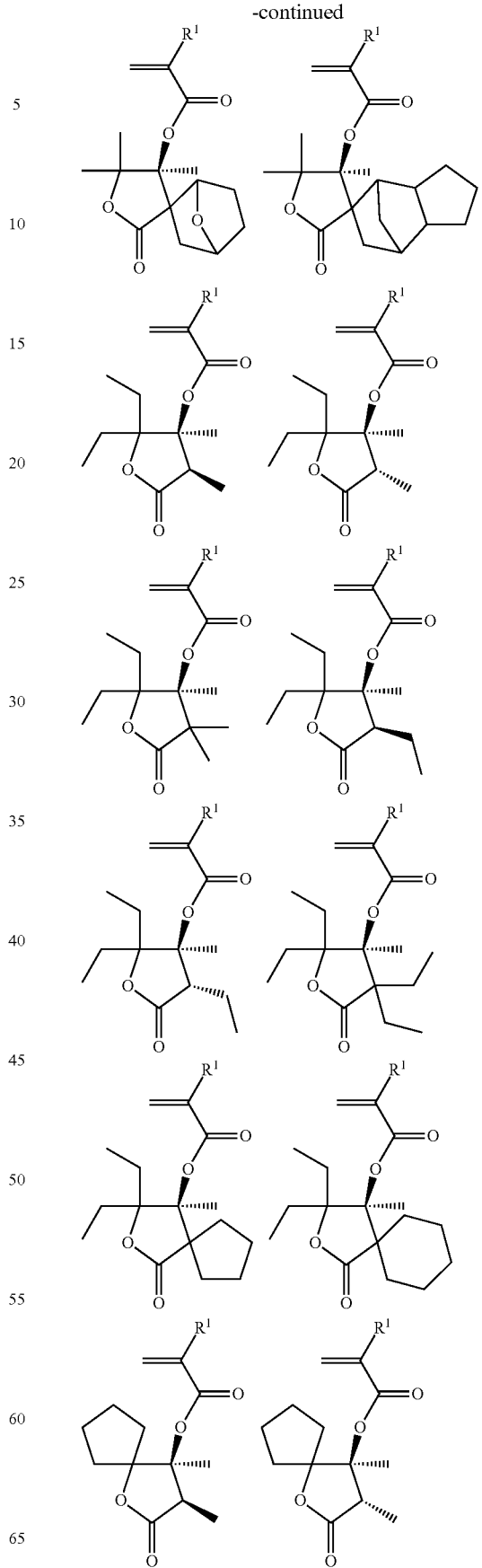

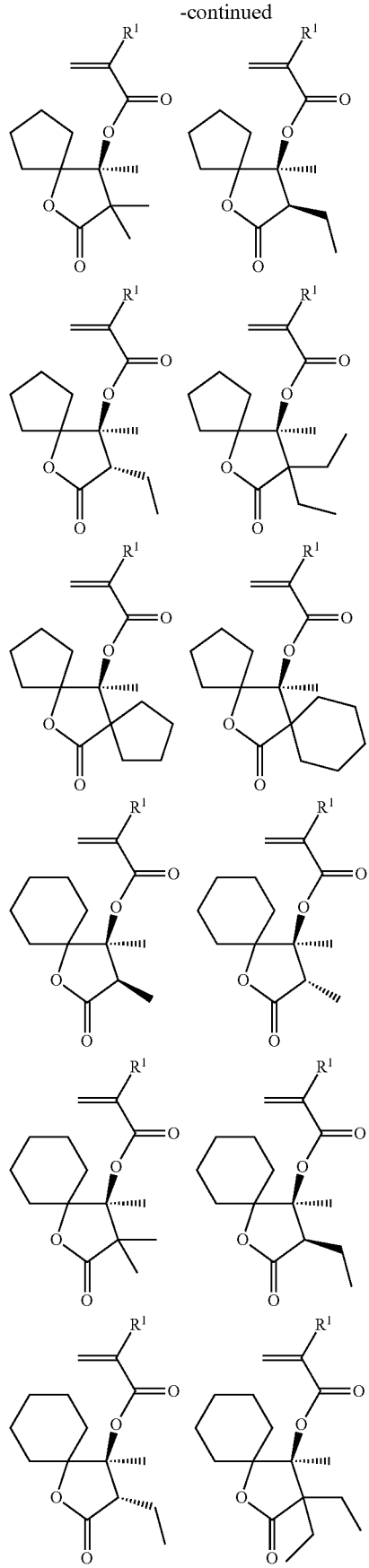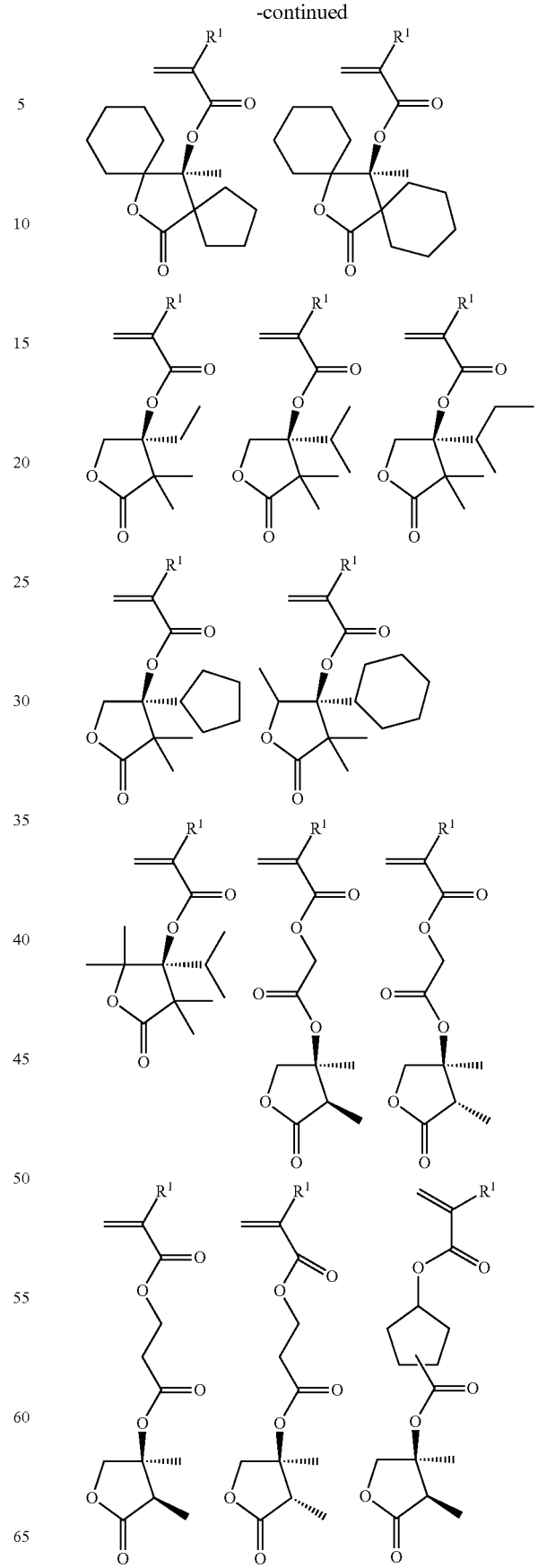

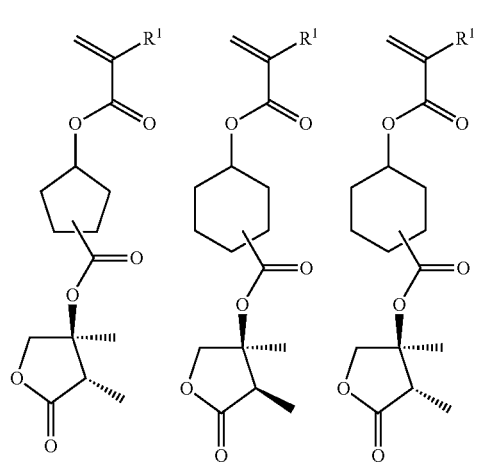
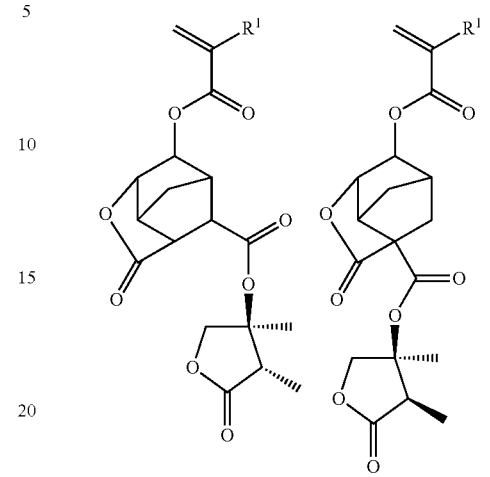
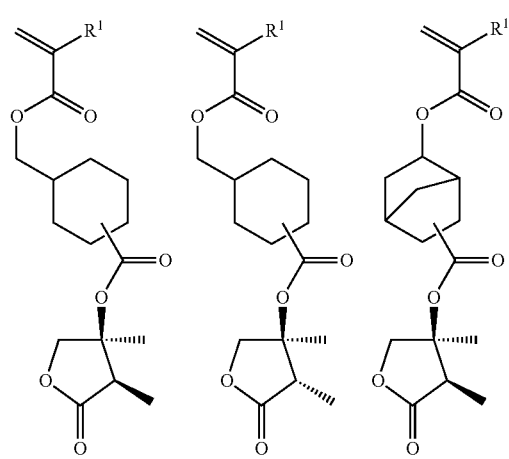
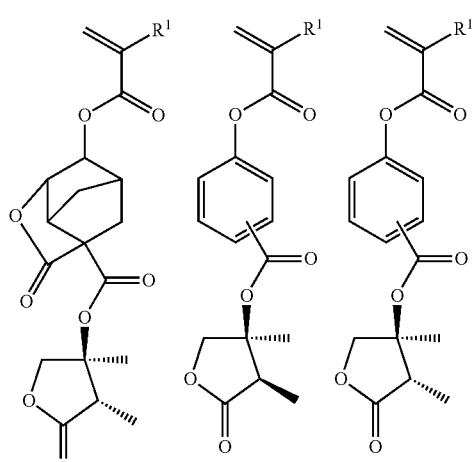
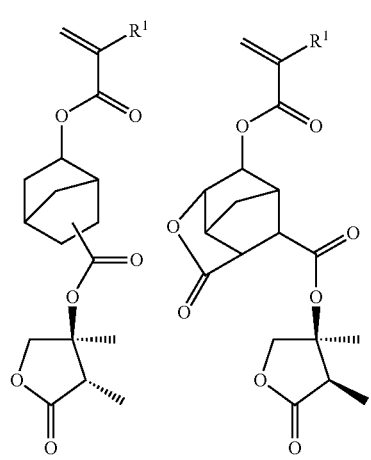
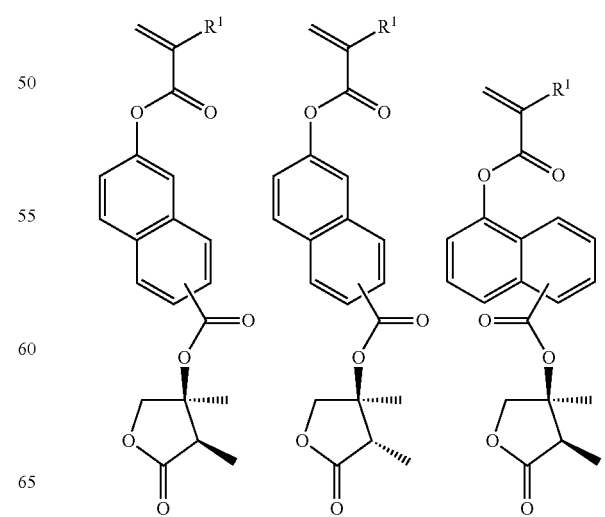

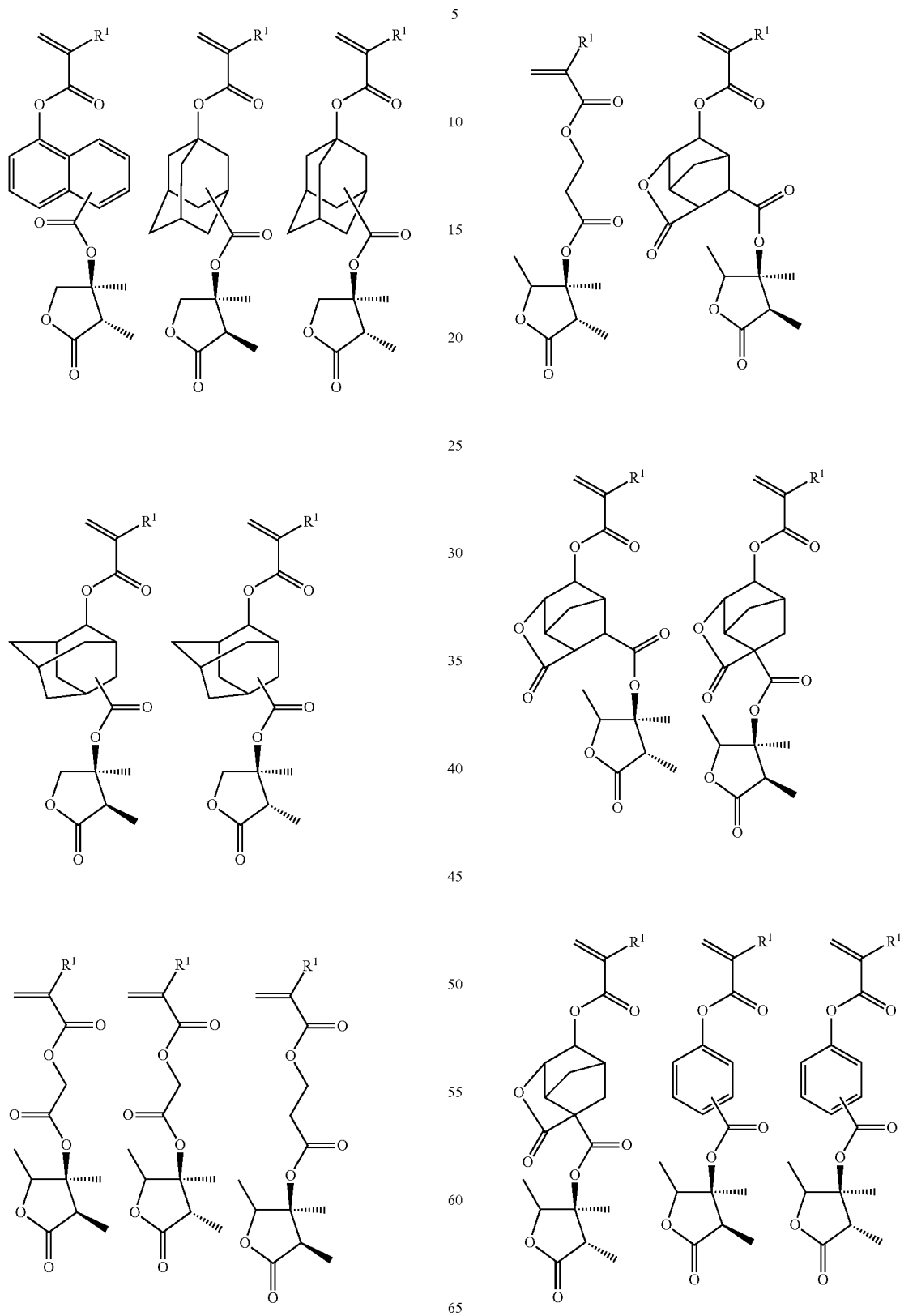

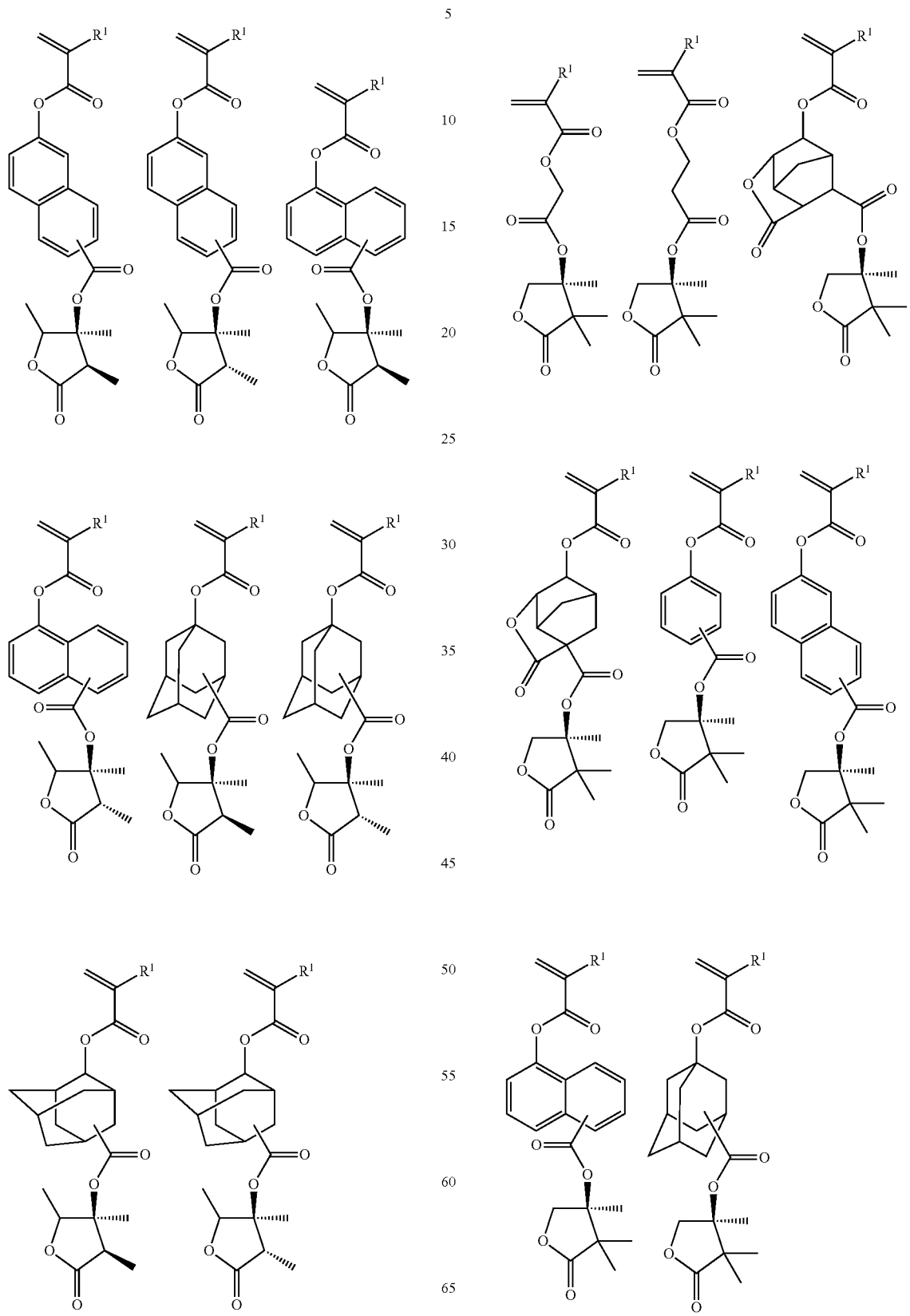

-continued

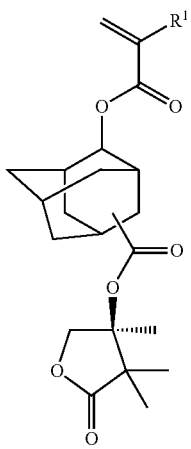

Herein $R^3$ is as defined above.

Now the method for preparing a monomer having formula (1) is described. The method of the first embodiment is defined as comprising the steps of reacting a compound having the general formula (9) with a base or a metal selected from Group 1A, 2A and 2B metals to form a metal enolate reagent, and reacting the metal enolate reagent with an acyloxyketone compound having the general formula (8).

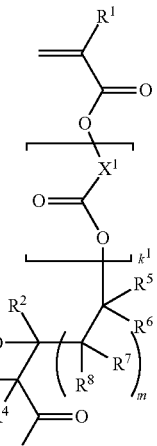

(9)

(8)

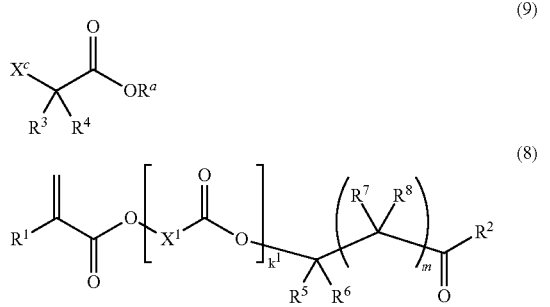

Herein $R^1$ to $R^8$, $X^1$, $k^1$, and m are as defined above. $X^c$ is hydrogen or halogen. $R^a$ is a straight or branched $C_1$-$C_{10}$ monovalent hydrocarbon group.

The method of the second embodiment is defined as comprising the steps of reacting a compound having the above formula (9) with a base or a metal selected from Group 1A, 2A and 2B metals to form a metal enolate reagent, reacting the metal enolate reagent with an acyloxyketone compound having the above formula (8), isolating the resulting intermediate having the general formula (12), and lactonizing the intermediate.

(12)

Herein $R^1$ to $R^8$, $X^1$, $k^1$, m, and $R^a$ are as defined above.

More particularly, the monomer having formula (1) may be prepared according to the reaction scheme shown below.

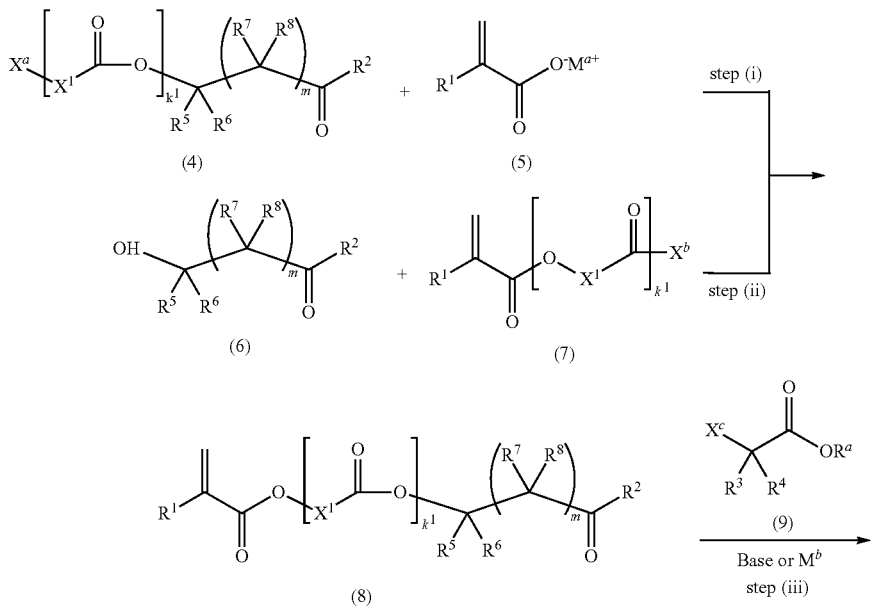

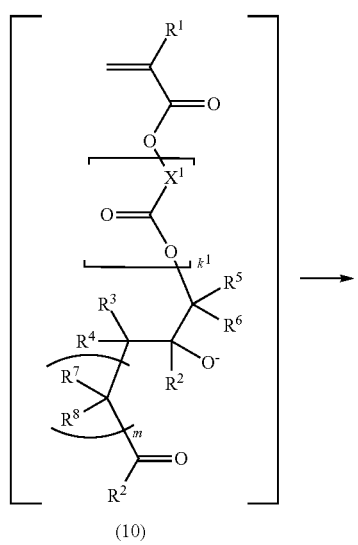 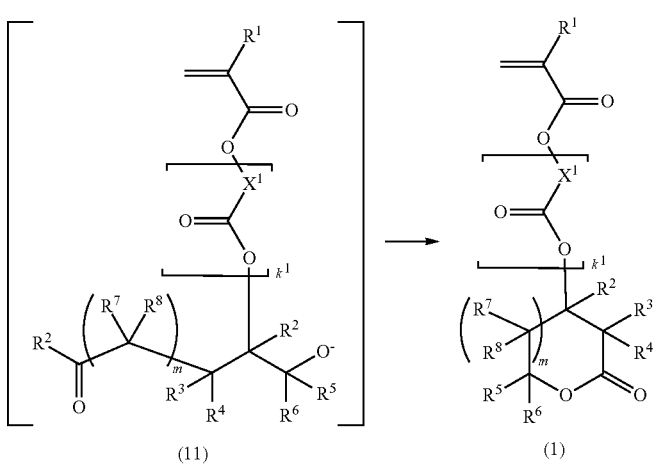

(10) (11) (1)

Herein $R^1$ to $R^8$, $X^1$, $k^1$, and m are as defined above. $X^a$ is halogen. $X^b$ is halogen, hydroxyl or —$OR^b$, wherein $R^b$ is methyl, ethyl or a group having the formula (11):

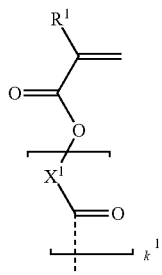

(11)

wherein $R^1$, $X^1$ and $k^1$ are as defined above, and the broken line denotes a valence bond. $X^c$ is hydrogen or halogen. $M^a$ is Li, Na, K, $Mg_{1/2}$, $Ca_{1/2}$ or substituted or unsubstituted ammonium. $M^b$ is a metal. $R^a$ is a straight or branched $C_1$-$C_{10}$ monovalent hydrocarbon group.

The method for preparing a monomer according to the above reaction scheme is described below.

Step (i) is a reaction of halo-ketone compound (4) with carboxylic acid salt compound (5) to form cyclization precursor (8). The reaction may readily run by a well-known procedure. The carboxylic acid salt compound (5) may be any of commercially available carboxylic acid salt compounds such as carboxylic acid metal salts. Alternatively, a corresponding carboxylic acid such as methacrylic acid or acrylic acid and a base are added to a reaction system where a carboxylic acid salt compound is formed therefrom. An appropriate amount of carboxylic acid salt compound (5) used is 0.5 to 10 moles, more preferably 1.0 to 3.0 moles per mole of halo-ketone compound (4). If the carboxylic acid salt compound is less than 0.5 mole, a large fraction of the reactant is left unreacted, with a substantial drop of yield. More than 10 moles of the carboxylic acid salt compound may be uneconomical because of an increase of material amount and a lowering of pot yield. In the alternative where a carboxylic acid salt compound is formed in situ from a corresponding carboxylic acid and a base, examples of the base used herein include amines such as ammonia, triethylamine, pyridine, lutidine, collidine, and N,N-dimethylaniline; hydroxides such as sodium hydroxide, potassium hydroxide, and tetramethylammonium hydroxide; carbonates such as potassium carbonate and sodium hydrogencarbonate; metals such as sodium; metal hydrides such as sodium hydride; metal alkoxides such as sodium methoxide and potassium tert-butoxide; organometallic compounds such as butyl lithium and ethylmagnesium bromide; and metal amides such as lithium diisopropylamide, which may be used alone or in admixture. An appropriate amount of the base used is 0.2 to 10 moles, more preferably 0.5 to 2.0 moles per mole of the corresponding carboxylic acid. If the base is less than 0.2 mole, a large fraction of the carboxylic acid may become waste, which is uneconomical. More than 10 moles of the base may promote side reactions, with a substantial drop of yield.

A solvent may be used for the reaction of step (i). Suitable solvents include hydrocarbons such as toluene, xylene, hexane and heptane; chlorinated solvents such as methylene chloride, chloroform, and dichloroethane; ethers such as diethyl ether, tetrahydrofuran and dibutyl ether; ketones such as acetone and 2-butanone; esters such as ethyl acetate and butyl acetate; nitriles such as acetonitrile; alcohols such as methanol and ethanol; aprotic polar solvents such as N,N-dimethylformamide, N,N-dimethylacetamide and dimethyl sulfoxide; and water, which may be used alone or in admixture. To the reaction system, a phase transfer catalyst such as tetrabutylammonium hydrogensulfate may be added. An appropriate amount of the phase transfer catalyst added is 0.0001 to 1.0 mole, more preferably 0.001 to 0.5 mole per mole of halo-ketone compound (4). Less than 0.0001 mole of the phase transfer catalyst may fail to exert catalytic effect whereas more than 1.0 mole may be uneconomical because of the increased catalyst cost.

The esterification reaction may be carried out preferably at a temperature in the range from −70° C. to approximately the boiling point of a particular solvent used. While an appropriate reaction temperature may be selected in accordance with other reaction conditions, a temperature in the range from 0° C. to approximately the boiling point of a particular solvent used is especially preferred. Since substantial side reactions may occur at elevated temperatures, it is crucial in achieving high yields to carry out the reaction at a temperature as low as possible within the range where reaction proceeds at a practically acceptable rate. It is desired for higher yields that the reaction time be determined by monitoring the progress of reaction by thin-layer chromatography (TLC) or gas chromatography (GC). The reaction time is usually about 30 minutes to about 40 hours. The precursor (8) may be recovered from the reaction mixture by ordinary aqueous work-up. If necessary, it can be purified by any standard technique such as distillation, recrystallization or chromatography.

Another route, step (ii) is a reaction of alcohol compound (6) with esterifying agent (7) to form cyclization precursor (8). The reaction may readily run by a well-known procedure. The preferred esterifying agent (7) is an acid chloride of formula (7) wherein $X^b$ is chlorine, or a carboxylic anhydride of formula (7) wherein $X^b$ is —$OR^b$, and $R^b$ is a group having formula (11):

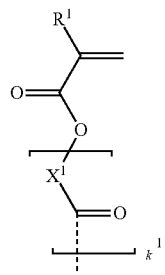

(11)

wherein $R^1$, $X^1$, and $k^1$ are as defined above. When an acid chloride such as methacrylic acid chloride or methacryloyloxyacetic acid chloride is used as esterifying agent (7), the reaction may be conducted in a solventless system or in a solvent (e.g., methylene chloride, acetonitrile, toluene or hexane) by adding alcohol compound (6), acid chloride, and a base (e.g., triethylamine, pyridine or 4-dimethylaminopyridine) in sequence or at the same time, and optional cooling or heating. An appropriate amount of the acid chloride used is 0.5 to 10 moles, more preferably 1.0 to 3.0 moles per mole of alcohol compound (6). An amount of the base used is preferably at least 0.5 moles per mole of alcohol compound (6) so that the base may also serve as solvent, and more preferably 1.0 to 5.0 moles per mole of alcohol compound (6). When a carboxylic anhydride such as methacrylic anhydride or methacryloyloxyacetic anhydride is used as esterifying agent (7), the reaction may be conducted by heating alcohol compound (6) and carboxylic anhydride in a solvent (e.g., toluene or hexane) in the presence of an acid catalyst and optionally removing water resulting from reaction out of the system. An appropriate amount of the carboxylic anhydride used is 1 to 5 moles per mole of alcohol compound (6). Examples of the acid catalyst used herein include mineral acids such as hydrochloric acid, sulfuric acid, nitric acid and perchloric acid and organic acids such as methanesulfonic acid, trifluoromethanesulfonic acid, p-toluenesulfonic acid and benzenesulfonic acid.

An appropriate amount of esterifying agent (7) used is 1 to 10 moles, more preferably 1 to 5 moles per mole of alcohol compound (6). Less than 1 mole of esterifying agent (7) is short for the progress of reaction so that a large fraction of alcohol compound (6) may be left unreacted, with a substantial drop of yield. More than 10 moles of the esterifying agent (7) may be uneconomical because of an increase of material amount and a lowering of pot yield.

The esterification reaction may be carried out preferably at a temperature in the range from −70° C. to approximately the boiling point of a particular solvent used. While an appropriate reaction temperature may be selected in accordance with other reaction conditions, a temperature in the range from 0° C. to approximately the boiling point of a particular solvent used is especially preferred. Since substantial side reactions may occur at elevated temperatures, it is crucial in achieving high yields to carry out the reaction at a temperature as low as possible within the range where reaction proceeds at a practically acceptable rate. It is desired for higher yields that the reaction time be determined by monitoring the progress of reaction by thin-layer chromatography (TLC) or gas chromatography (GC). The reaction time is usually about 30 minutes to about 40 hours. The precursor (8) may be recovered from the reaction mixture by ordinary aqueous work-up. If necessary, it can be purified by any standard technique such as distillation, recrystallization or chromatography.

Step (iii) is to obtain monomer (1) in one-pot through reaction of a corresponding ester of formula (9) wherein $X^c$ is hydrogen or halo-ester of formula (9) wherein $X^c$ is halogen with a base or metal to form a metal enolate reagent, effecting nucleophilic addition reaction of the enolate to the ketone site of acyloxy-ketone compound (8), forming intermediate (10) and then intermediate (11).

Examples of the base used herein include, but are not limited to, metal amides such as sodium amide, potassium amide, lithium diisopropylamide, potassium diisopropylamide, lithium dicyclohexylamide, potassium dicyclohexylamide, lithium 2,2,6,6-tetramethylpiperidine, lithium bistrimethylsilylamide, sodium bistrimethylsilylamide, potassium bistrimethylsilylamide, lithium isopropylcyclohexylamide, magnesium diisopropylamide bromide; alkoxides such as sodium methoxide, sodium ethoxide, lithium methoxide, lithium ethoxide, lithium tert-butoxide, and potassium tert-butoxide; inorganic hydroxides such as sodium hydroxide, lithium hydroxide, potassium hydroxide, barium hydroxide, and tetra-n-butylammonium hydroxide; inorganic carbonates such as sodium carbonate, sodium hydrogencarbonate, lithium carbonate, and potassium carbonate; metal hydrides such as boran, alkylboran, sodium hydride, lithium hydride, potassium hydride, and calcium hydride; alkyl metal compounds such as trityl lithium, trityl sodium, trityl potassium, methyl lithium, phenyl lithium, sec-butyl lithium, tert-butyl lithium, and ethylmagnesium bromide. The metal used herein is selected from Group 1A, 2A and 2B metals such as lithium, sodium, potassium, magnesium and zinc. It is noted that reaction using halo-ester and zinc is known as Reformatsky reaction. Among others, Reformatsky reaction is preferred because of possible preparation and handling of metal enolate reagent under mild temperature conditions and a high selectivity of reaction at the ketone site of acyloxy-ketone (8).

The Reformatsky reaction may be conducted by a well-known procedure. Since the previous preparation of Reformatsky reagent may invite a drop of yield and by-product formation, a procedure of simultaneously adding dropwise halo-ester compound (9) and cyclization precursor or ketone (8) to a suspension of metallic zinc is preferred. It is believed that if Reformatsky reagent has been pre-formed, the Reformatsky reagent is consumed by reaction with the reactant, halo-ester compound (9), resulting in a drop of yield. An appropriate amount of cyclization precursor (8) used is 0.5 to 10 moles, more preferably 0.8 to 3.0 moles per mole of the reactant, halo-ester compound (9). If precursor (8) is less than 0.5 mole, a large fraction of the reactant may be left unreacted, with a substantial drop of yield. More than 10 moles of precursor (8) may be uneconomical because of an increase of material amount and a lowering of pot yield.

Likewise, in the embodiment wherein ester (9) wherein $X^c$ is hydrogen is reacted with a base to form a metal enolate reagent, which is subjected to reaction with precursor (8), an appropriate amount of cyclization precursor (8) used is 0.5 to 10 moles, more preferably 0.8 to 3.0 moles per mole of the reactant, ester (9). An appropriate amount of the base or metal used is 0.8 to 5 moles, more preferably 0.8 to 2.0 moles per mole of ester (9). If the base or metal is less than 0.8 mole, a large fraction of the reactant is left unreacted, with a substantial drop of yield. More than 5 moles of the base or metal may be uneconomical because of an increase of material amount and a lowering of pot yield. The reaction may be conducted in a solvent. Suitable solvents include hydrocarbons such as benzene, toluene, xylene, hexane, and heptane; chlorinated solvents such as methylene chloride, chloroform, and dichloroethane; ethers such as diethyl ether, tetrahydrofuran, and dibutyl ether; nitriles such as acetonitrile; alcohols such as methanol and ethanol; aprotic polar solvents such as N,N-dimethylformamide, N,N-dimethylacetamide and dimethyl sulfoxide; and water, which may be used alone or in admixture. Particularly in the case of Reformatsky reaction, the preferred procedure is by dissolving zinc in a solvent and admitting halo-ester (9) to the solution, the solvent being selected from ethers such as ethyl ether, tetrahydrofuran and dibutyl ether and hydrocarbons such as benzene, toluene, xylene, hexane and heptane.

For the above reaction, an appropriate reaction temperature may be selected in accordance with other reaction conditions. A temperature in the range of 30 to 80° C. is preferred because full reaction may not take place at lower temperature whereas side reactions may become noticeable at higher temperature. The reaction time is determined as appropriate for yield improvement by monitoring the reaction process by thin-layer chromatography (TLC) or gas chromatography (GC). The reaction time is usually about 30 minutes to about 2 hours because long-term aging allows for anionic polymerization to invite a drop of monomer yield. In step (iii), basically, a series of reactions run from addition intermediate (10) such that intermediate (11) forms via rearrangement of ester site, and lactonization ensues to form the desired monomer (1). Monomer (1) may be recovered from the reaction mixture by ordinary aqueous work-up. If necessary, the monomer may be purified by standard techniques like distillation, recrystallization and chromatography.

When a bulky ester such as tert-butyl ester is used as ester (9), the reaction of step (iii) may terminate at the stage of intermediate (10). This is undesirable for the one-pot synthesis of monomer (1) because a drop of yield, difficulty of purification and other problems arise. In this case, the problems may be overcome by isolating hydroxy-ester (10') and subjecting it to acid treatment. For example, monomer (1) is obtained from cyclization precursor (8) according to the following reaction scheme.

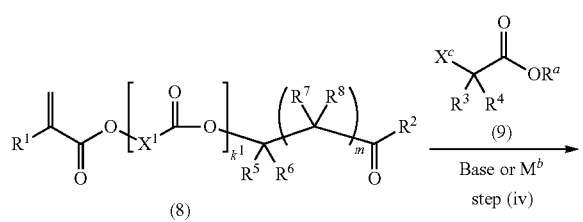

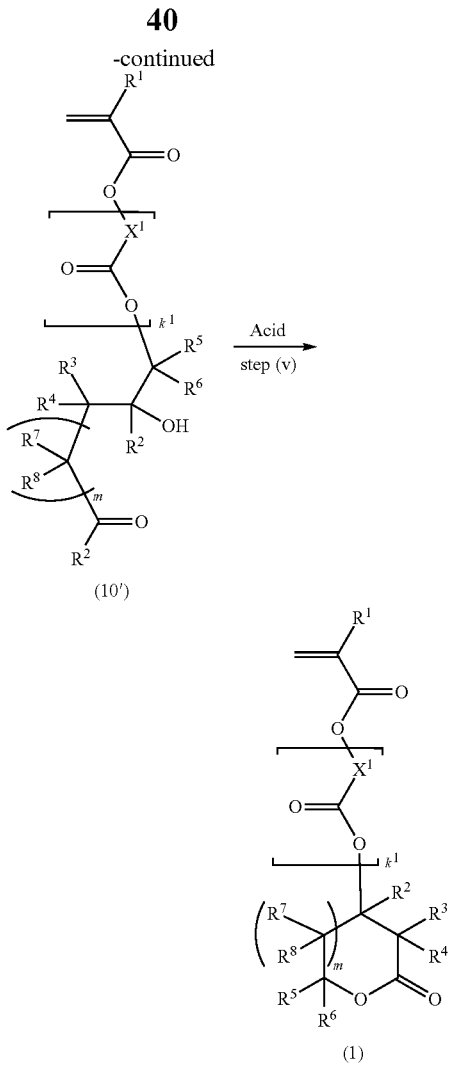

Herein $R^1$ to $R^8$, $X^1$, $X^c$, $k^1$, m, $R^a$, and $M^b$ are as defined above.

Like step (iii), step (iv) is addition reaction of acyloxy-ketone compound (8) and ester compound (9) with the aid of a base or metal. Preferably Reformatsky reaction is utilized. Reaction may be carried out under the same conditions as in step (iii). Once the reaction terminates at the stage of intermediate (10), hydroxy-ester compound (10') may be isolated from the reaction mixture by ordinary aqueous work-up. If necessary, the compound may be purified by standard techniques like distillation, recrystallization and chromatography.

Step (v) is acid treatment of hydroxy-ester compound (10') into the desired monomer (1). Step (v) is carried out by diluting hydroxy-ester compound (10') with a solvent, adding an acid, heating and stirring the mixture for reaction. Suitable solvents include hydrocarbons such as toluene, xylene, hexane and heptane; chlorinated solvents such as methylene chloride, chloroform, and dichloroethane; ethers such as diethyl ether, tetrahydrofuran and dibutyl ether; ketones such as acetone and 2-butanone; esters such as ethyl acetate and butyl acetate; nitriles such as acetonitrile; alcohols such as methanol and ethanol; aprotic polar solvents such as N,N-dimethylformamide, N,N-dimethylacetamide and dimethyl sulfoxide; and water, which may be used alone or in admixture. Notably, the reaction may also be conducted in a solventless system.

Suitable acids include mineral acids such as hydrochloric acid, sulfuric acid, nitric acid and perchloric acid, organic acids such as methanesulfonic acid, trifluoromethanesulfonic acid, p-toluenesulfonic acid, and benzenesulfonic acid, and Lewis acids such as boron trifluoride, trimethylsilyl triflate, aluminum chloride, magnesium chloride, iron chloride, zinc chloride, and titanium chloride. An appropriate amount of the acid used is 0.001 to 5 moles, more preferably 0.01 to 0.5 mole per mole of the reactant, hydroxy-ester compound (10'). Less than 0.001 mole of the acid may invite an economic disadvantage because of a slow reaction rate and longer reaction time. More than 5 moles may incur side reactions due to strong acidity, with a drop of yield.

For the acid treatment, an appropriate reaction temperature may be selected in accordance with other reaction conditions. In most cases, a temperature of 40 to 70° C. is preferred because reaction does not take place at lower temperatures. The reaction time is determined as appropriate for yield improvement by monitoring the reaction process by thin-layer chromatography (TLC) or gas chromatography (GC). The reaction time is usually about 2 hours to about 1 day. At the end of reaction, monomer (1) may be recovered from the reaction mixture by ordinary aqueous work-up. If necessary, the monomer may be purified by standard techniques like distillation, recrystallization and chromatography.

The monomer thus obtained is used to form a polymer. Specifically, a polymer comprising recurring units having the following formula may be synthesized by dissolving the inventive monomer and an optional monomer(s) having a polymerizable double bond in an organic solvent, adding a radical polymerization initiator thereto, and effecting heat polymerization.

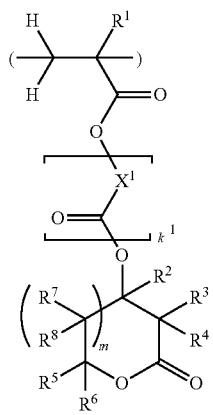

Herein $R^1$ to $R^8$, $X^1$, $k^1$, and m are as defined above.

Examples of the organic solvent which can be used for polymerization include toluene, benzene, tetrahydrofuran, diethyl ether, dioxane, cyclohexane, cyclopentane, methyl ethyl ketone, and γ-butyrolactone (GBL). Examples of the polymerization initiator used herein include 2,2'-azobisisobutyronitrile (AIBN), 2,2'-azobis(2,4-dimethylvaleronitrile), dimethyl 2,2-azobis(2-methylpropionate), benzoyl peroxide, and lauroyl peroxide. Preferably the system is heated at 50 to 80° C. for polymerization to take place. The reaction time is 2 to 100 hours, preferably 5 to 20 hours.

The resulting polymer may be advantageously used as base resin in chemically amplified positive and negative resist compositions. In forming patterns using these resist compositions, any well-known methods may be used.

EXAMPLE

Examples, Reference Examples and Comparative Examples are given below by way of illustration and not by way of limitation. The abbreviation "pbw" is parts by weight. For all polymers, Mw and Mn are determined versus polystyrene standards by GPC using tetrahydrofuran (THF) solvent.

Synthesis of Monomers

A series of monomers and ketone compounds as monomer precursor were synthesized according to the following formulation.

Example 1

Synthesis of Monomers 1, 2 and 3

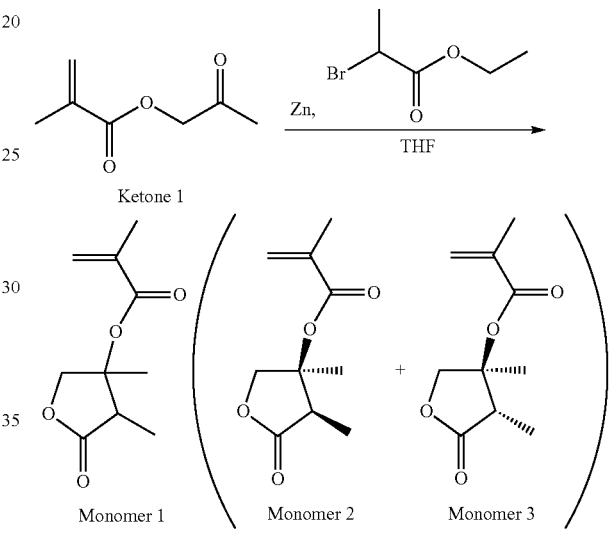

Example 1-1

Synthesis of Monomer 1

In a nitrogen atmosphere, 79.2 g of zinc powder was dissolved in 660 mL of THF. Then 4.93 g of 1,2-dibromoethane and 1.86 g of trimethylsilyl chloride were added to the solution, which was heated and stirred for activating zinc. To the activated zinc-THF solution, a mixture of 200.8 g of Ketone 1, which had been prepared by a well-known method, 182.7 g of ethyl 2-bromopropionate, and 330 mL of THF was added dropwise at 45° C., followed by heating and stirring at 45° C. for 2 hours. Under ice cooling, 530 g of 10% aqueous hydrochloric acid was added. This was followed by standard aqueous workup and solvent distillation. The product was purified by distillation, obtaining 132.1 g of Monomer 1 (yield 63%, isomer ratio 61:39).

Example 1-2

Synthesis of Monomers 2 and 3

Monomer 1 obtained in Example 1-1, 132 g, was added to a mixture of 65 g of ethyl acetate and 200 g of hexane. Recrystallization at −10° C. gave 68.2 g of Monomer 2 (isomer ratio 97:3). By concentrating the mother liquid under reduced pressure and purifying by silica gel column chromatography, 45.7 g of Monomer 3 was obtained (isomer ratio 100:0).

Monomer 2
melting point: 76.0-76.3° C.
boiling point: 69° C./10 Pa
IR (D-ATR): ν=2981, 2962, 2942, 1780, 1768, 1708, 1634, 1475, 1447, 1379, 1331, 1302, 1254, 1212, 1178, 1165, 1152, 1127, 1102, 1063, 1032, 1010, 947, 870, 817, 721, 658, 564 cm$^{-1}$
$^1$H-NMR (600 MHz in DMSO-$d_6$, only major isomer):
δ=1.12 (3H, d), 1.61 (3H, s), 1.83 (3H, s), 2.89 (1H, q), 4.24 (1H, d), 4.72 (1H, d), 5.69 (1H, s), 5.96 (1H, s) ppm Monomer 3
boiling point: 69° C./10 Pa
IR (D-ATR): ν=2983, 1785, 1716, 1637, 1449, 1389, 1333, 1309, 1286, 1220, 1169, 1146, 1131, 1096, 1055, 1014, 940, 863, 814, 652 cm$^{-1}$
$^1$H-NMR (600 MHz in DMSO-$d_6$):
δ=1.15 (3H, d), 1.45 (3H, s), 1.85 (3H, s), 3.07 (1H, q), 4.42 (1H, d), 4.48 (1H, d), 5.71 (1H, s), 6.04 (1H, s) ppm Example 2

Synthesis of Monomer 4

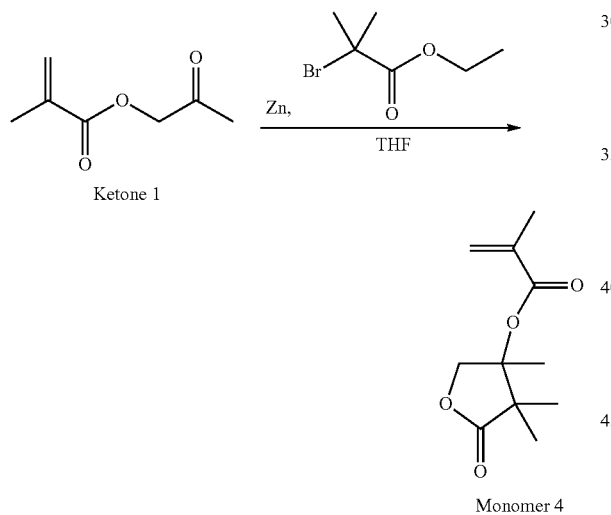

In a nitrogen atmosphere, 92.4 g of zinc powder was dissolved in 800 mL of THF. Then 5.53 g of 1,2-dibromoethane and 1.92 g of trimethylsilyl chloride were added to the solution, which was heated and stirred for activating zinc. To the activated zinc-THF solution, a mixture of 178.1 g of Ketone 1, 241.6 g of ethyl 2-bromoisobutyrate, and 400 mL of THF was added dropwise at 50° C., followed by heating and stirring at 50° C. for 1.5 hours. Under ice cooling, 584 g of 10% aqueous hydrochloric acid was added. This was followed by standard aqueous workup and solvent distillation. The product was purified by distillation, obtaining 156.2 g of Monomer 4 (yield 58%).
boiling point: 75° C./10 Pa
IR (D-ATR): ν=2982, 2940, 1785, 1717, 1637, 1485, 1468, 1395, 1380, 1328, 1304, 1286, 1233, 1159, 1141, 1118, 1102, 1024, 944, 843, 814, 659 cm$^{-1}$
$^1$H-NMR (600 MHz in DMSO-$d_6$):
δ=1.14 (3H, s), 1.18 (3H, s), 1.50 (3H, s), 1.84 (3H, s), 4.45 (1H, d), 4.71 (1H, d), 5.69 (1H, s), 5.98 (1H, s) ppm Example 3-1

Synthesis of Monomer 5

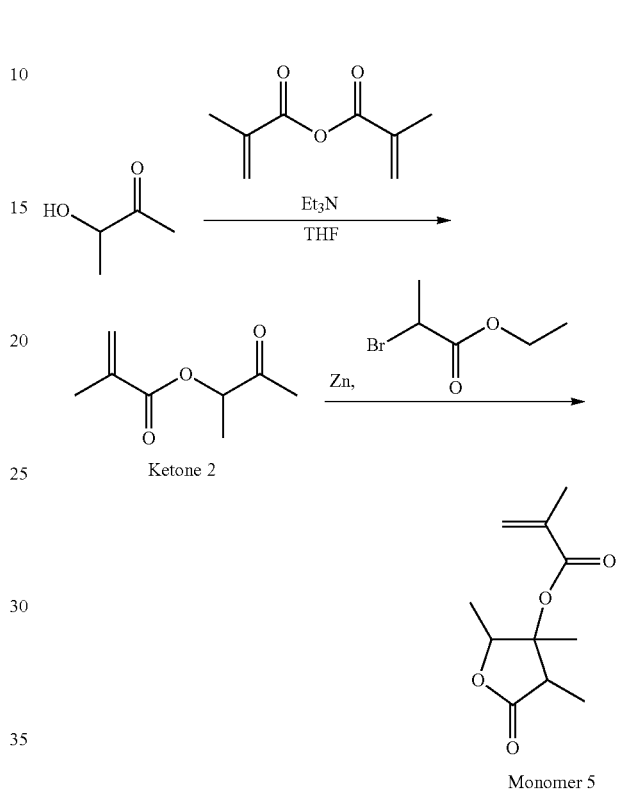

Example 3-1-1

Synthesis of Ketone 2

In a nitrogen atmosphere, 200 g of acetoin and 269.2 g of methacrylic anhydride were dissolved in 1,000 mL of THF. At room temperature, 212 g of triethylamine was added dropwise to the solution, which was stirred at room temperature for 24 hours. This was followed by standard aqueous workup and solvent distillation. The product was purified by distillation, obtaining 212.7 g of Ketone 2 (yield 74%).
boiling point: 63° C./900 Pa
IR (D-ATR): ν=2988, 2932, 1717, 1638, 1452, 1360, 1329, 1309, 1162, 1094, 1047, 1009, 945, 861, 815, 657 cm$^{-1}$
$^1$H-NMR (600 MHz in DMSO-$d_6$):
δ=1.36 (3H, d), 1.89 (3H, s), 2.13 (3H, s), 5.09 (1H, q), 5.74 (1H, m), 6.09 (1H, m) ppm Example 3-1-2

Synthesis of Monomer 5

In a nitrogen atmosphere, 33.9 g of zinc powder was dissolved in 250 mL of THF. Then 2.3 g of 1,2-dibromoethane and 0.9 g of trimethylsilyl chloride were added to the solution, which was heated and stirred for activating zinc. To the activated zinc-THF solution, a mixture of 82.0 g of Ketone 2, 98.5 g of ethyl 2-bromopropionate, and 150 mL of THF was added dropwise at 55° C., followed by heating and stirring at 55° C. for 1.5 hours. Under ice cooling, 227 g of 10% aqueous hydrochloric acid was added. This was followed by standard aqueous workup and solvent distillation. The product was purified by silica gel column chromatography, obtaining 53.1 g of Monomer 5 (yield 48%, isomer ratio 57:32:11:0).

IR (D-ATR): ν=2985, 2944, 1782, 1717, 1637, 1452, 1386, 1328, 1302, 1208, 1167, 1135, 1096, 1072, 1052, 1012, 944, 888, 814, 663 cm$^{-1}$ $^1$H-NMR (600 MHz in DMSO-d$_6$, only major isomer):
δ=1.13 (3H, d), 1.30 (3H, d), 1.57 (3H, s), 1.83 (1H, m), 3.09 (1H, q), 4.96 (1H, q), 5.68 (1H, m), 5.95 (1H, m) ppm Example 3-2

Synthesis of Monomer 5 Via Another Route

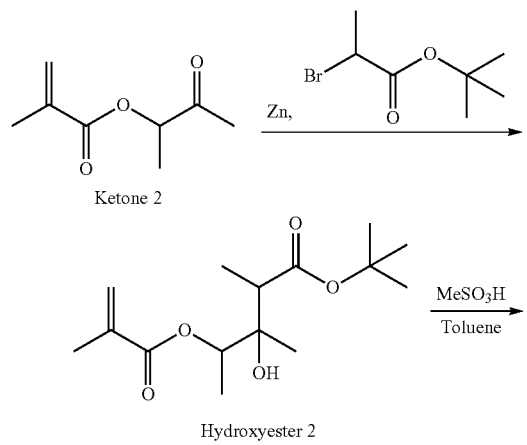

Example 3-2-1

Synthesis of Hydroxyester 2

16.4 g of 1,2-dibromoethane was added to a suspension of 250.6 g of zinc in 2,900 mL of THF, which was stirred under reflux conditions for 1 hour. The reactor was cooled to an internal temperature of 40° C., after which 7.6 g of chlorotrimethylsilane was added to the suspension, which was stirred for 10 minutes. To the suspension at 30° C., a solution of 2.653 g of Ketone 2, 728.5 g of t-butyl 2-bromopropionate, and 16.4 g of 1,2-dibromoethane in 750 mL of THF was added dropwise. Until the end of dropwise addition, the temperature was kept below 40° C. by optional cooling. This was followed by stirring at 35° C. for 1 hour and cooling. With the temperature kept below 20° C., 1,050 g of 20% aqueous hydrochloric acid was added dropwise to quench the reaction. Stirring was continued at room temperature for some time until zinc was dissolved. The reaction mixture was extracted with 2,000 mL of toluene, followed by standard aqueous workup and solvent distillation. The product was purified by distillation, obtaining 716.3 g of Hydroxyester 2 (yield 69%, isomer ratio 40:39:18:3).

boiling point: 80° C./10 Pa $^1$H-NMR (600 MHz in DMSO-d$_6$, only major isomer):
δ=1.05 (3H, d), 1.09 (3H, s), 1.17 (3H, d), 1.33 (9H, s), 1.87 (3H, s), 2.46 (1H, q), 4.58 (1H, s), 4.87 (1H, m), 5.61 (1H, s), 6.08 (1H, s) ppm Example 3-2-2

Synthesis of Monomer 5

At room temperature, 80 g of methanesulfonic acid was added dropwise to a mixture of 800 g of Hydroxyester 2 and 800 g of toluene. The mixture was heated at an internal temperature of 50° C. and stirred for 12 hours. The reaction solution was cooled after the completion of reaction was confirmed. 880 g of 10% aqueous solution of sodium hydrogencarbonate was added dropwise to quench the reaction. This was followed by standard aqueous workup and solvent distillation. The product was purified by distillation, obtaining 466.8 g of Monomer 5 (yield 77%, isomer ratio 40:28:18:14).

boiling point: 73° C./5 Pa

Example 4

Synthesis of Monomer 6

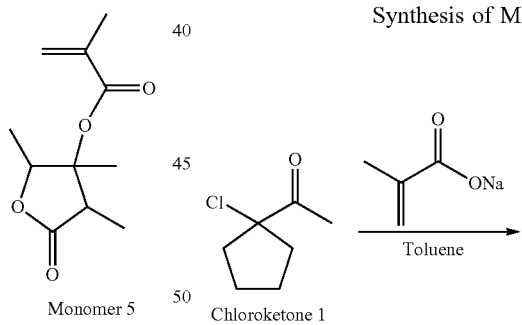

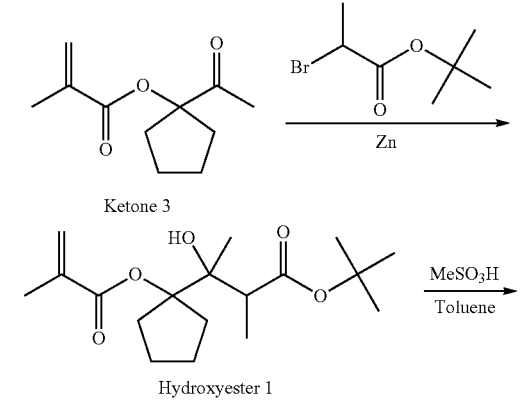

47
-continued

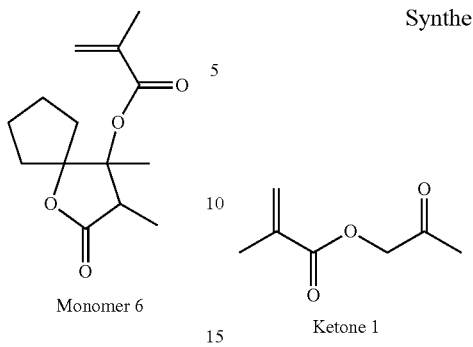

Monomer 6

Example 4-1

Synthesis of Ketone 3

Chloroketone 1, 339 g, was added to a suspension of 300 g of sodium methacrylate in 3,000 mL of toluene, which was aged at 90° C. for 40 hours. The reaction solution was cooled, to which 1,000 mL of water was added to quench the reaction. This was followed by standard aqueous workup and solvent distillation. Vacuum distillation gave 409 g of Ketone 3 (yield 90%).

Example 4-2

Synthesis of Hydroxyester 1

In a nitrogen atmosphere, 28.8 g of zinc powder was dissolved in 280 mL of THF. Then 1.8 g of 1,2-dibromoethane and 0.7 g of trimethylsilyl chloride were added to the solution, which was heated and stirred for activating zinc. To the activated zinc-THF solution, a mixture of 92.0 g of Ketone 3, 76.8 g of tert-butyl 2-bromopropionate, and 140 mL of THF was added dropwise at 60° C., followed by heating and stirring at 60° C. for 1.0 hour. Under ice cooling, 400 g of a saturated aqueous solution of ammonium chloride was added. This was followed by standard aqueous workup and solvent distillation. As crude product, 134.9 g of Hydroxyester 1 was obtained (yield 73%, isomer ratio 55:45).

Example 4-3

Synthesis of Monomer 6

Methanesulfonic acid, 10 g, was added to a mixture of 100.2 g of crude Hydroxyester 1 and 100 g of toluene, which was heated and stirred at 50° C. for 10 hours. The reaction solution was cooled, after which 100 g of a saturated aqueous solution of sodium hydrogencarbonate was added. This was followed by standard aqueous workup and solvent distillation. Vacuum distillation gave 40.3 g of Monomer 6 (yield 78%, isomer ratio 55:45).

48

Example 5

Synthesis of Monomer 7

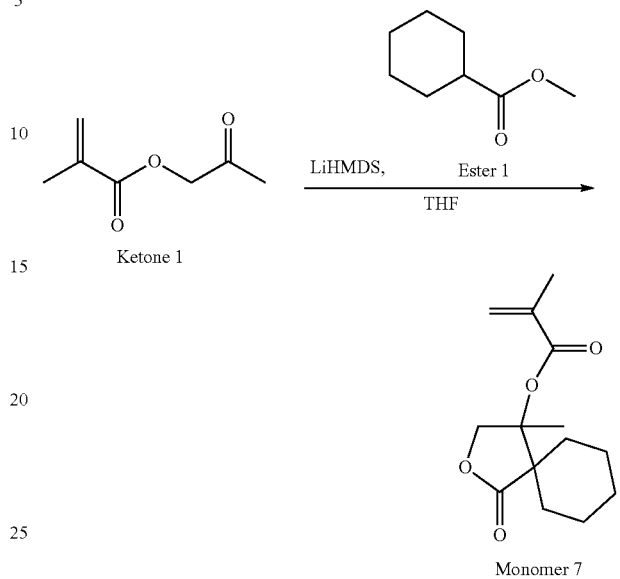

A THF solution (78 mL) of 1.3M lithium hexamethyldisilazide was cooled at −50° C., to which 14.8 g of Ester 1 was added dropwise. Stirring was continued at the temperature for 10 minutes. To the resulting enolate solution kept at −40° C., a solution of 16.3 g of Ketone 1 in 15 mL of THF was added dropwise. Stirring was continued at −40° C. for 30 minutes. With cooling interrupted, the solution was warmed up to room temperature over 1 hour. It was heated at 40° C. and stirred for 1 hour. The solution was cooled again, after which 40 g of 10 wt % aqueous hydrochloric acid was added to quench the reaction. This was followed by standard aqueous workup and solvent distillation. The product was purified by silica gel column chromatography, obtaining 10.2 g of Monomer 7. Yield 40%.

Example 6

Synthesis of Monomer 8

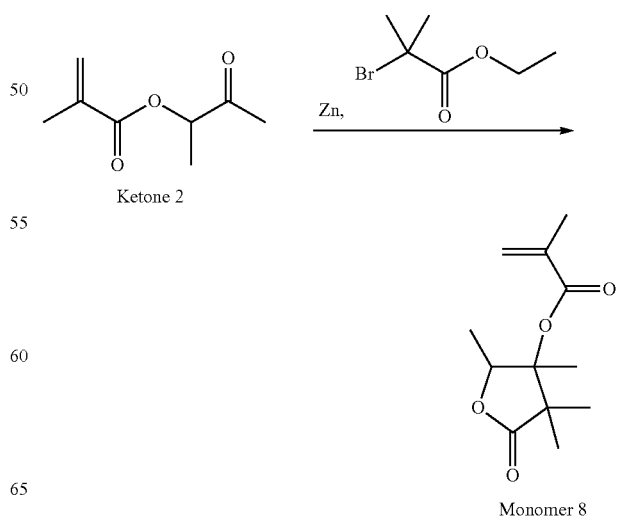

By following the same procedure as in Example 2 aside from using Ketone 2 instead of Ketone 1, there was obtained 33.7 g of Monomer 8. Yield 51%.

Example 7

Synthesis of Monomer 9

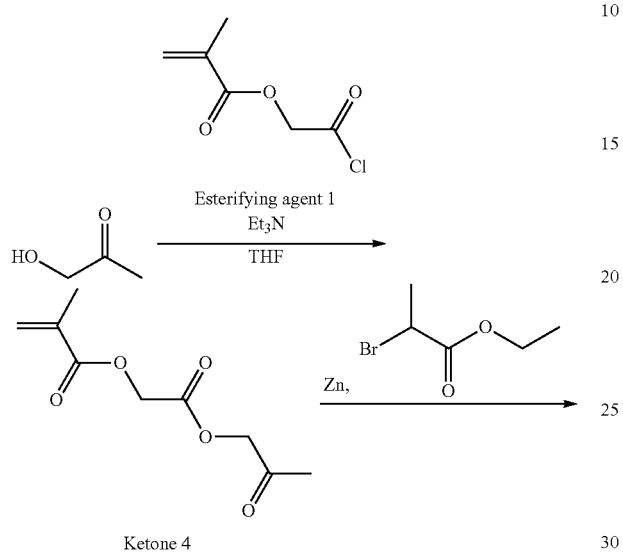

Ketone 4

Monomer 9

Example 7-1

Synthesis of Ketone 4

In a nitrogen atmosphere, 20 g of hydroxyacetone, 48.1 g of Esterifying agent 1, and 0.5 g of 4-dimethylaminopyridine were dissolved in 100 mL of acetonitrile. At room temperature, 35.5 g of triethylamine was added dropwise to the solution, which was stirred at room temperature for 12 hours. This was followed by standard aqueous workup and solvent distillation. The product was purified by distillation, obtaining 44.5 g of Ketone 4 (yield 85%).

Example 7-2

Synthesis of Monomer 9

By following the same procedure as in Example 1-1 aside from using Ketone 4 instead of Ketone 1, there was obtained 28.4 g of Monomer 9. Yield 46%.

Example 8

Synthesis of Monomer 10

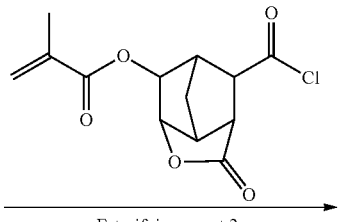

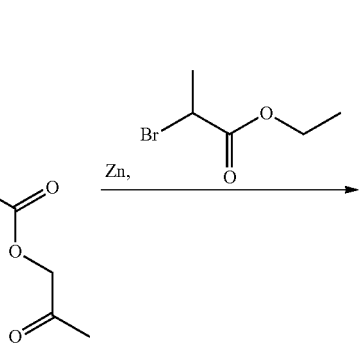

Ketone 5

Monomer 10

By following the same procedure as in Example 7 aside from using Esterifying agent 2 instead of Esterifying agent 1, there was obtained 20.3 g of Monomer 10. Yield 41%.

Example 9

Synthesis of Monomer 11

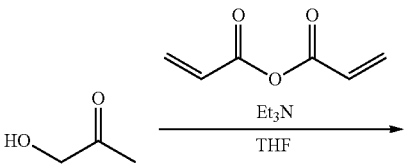

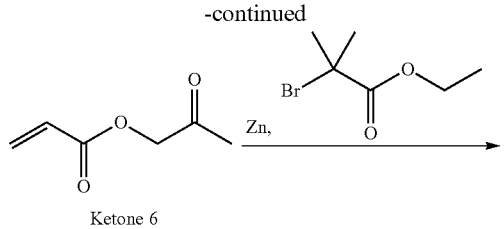

Ketone 6

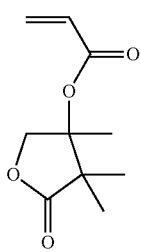

Monomer 11

The same procedure as in Example 3 was repeated aside from using hydroxyacetone, acrylic anhydride and ethyl 2-bromoisobutyrate. There was obtained 17.4 g of Monomer 11 in a two-step yield of 37%.

Example 10

Synthesis of Monomer 12

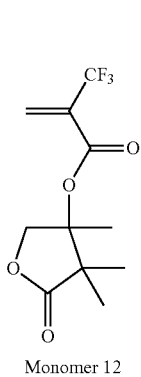

Ketone 7

Monomer 12

The same procedure as in Example 3 was repeated aside from using hydroxyacetone, α-trifluoromethylacrylic anhydride and ethyl 2-bromoisobutyrate. There was obtained 13.8 g of Monomer 12 in a two-step yield of 35%.

A list of Monomers 1 to 12 obtained in Examples are shown by the structural formula.

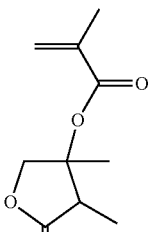 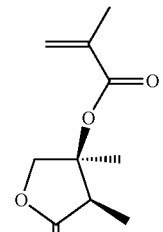 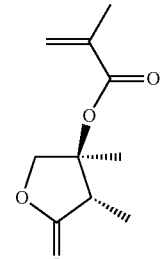

Monomer 1   Monomer 2   Monomer 3

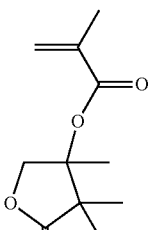 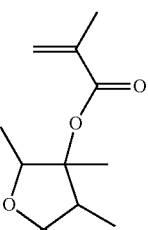

Monomer 4   Monomer 5

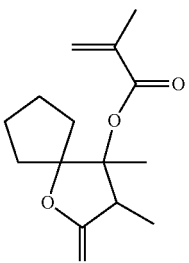 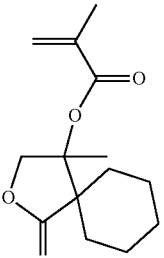

Monomer 6   Monomer 7

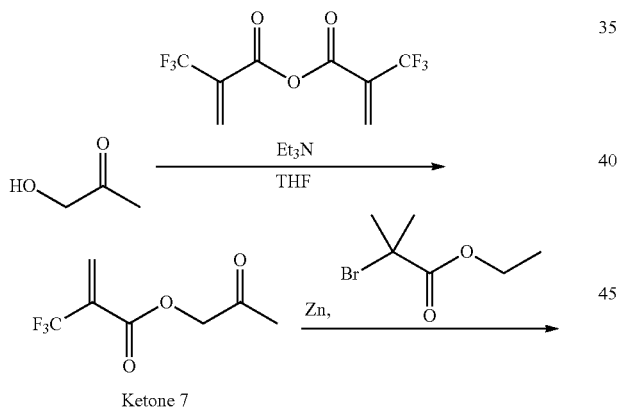

Monomer 8

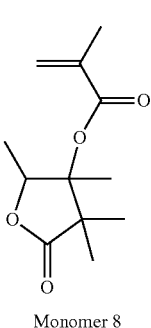 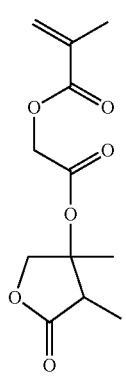

Monomer 9

-continued

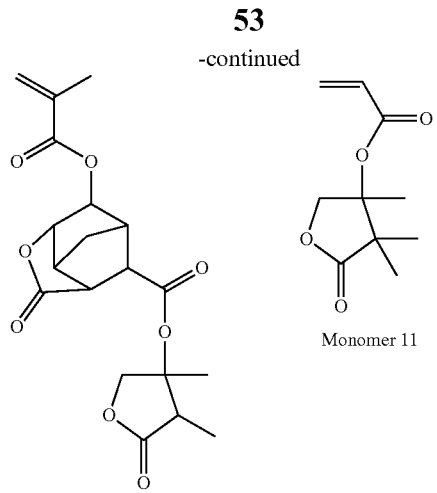

Monomer 10

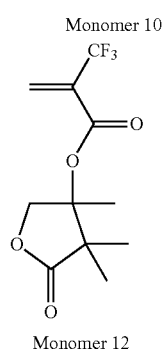

Monomer 12

Monomer 11

Reference Example

Synthesis of Polymers

A series of polymers for use in resist compositions were synthesized by dissolving selected monomers in propylene glycol monomethyl ether acetate (PGMEA), copolymerization reaction, crystallizing from methanol, repeatedly washing with methanol, isolation and drying. The composition of a polymer was analyzed by $^1$H-NMR spectroscopy, and the Mw and Mw/Mn determined by GPC. The polymers are designated Polymers 1 to 13 and Comparative Polymers 1 to 6.

Polymer 1
 Mw=9,600
 Mw/Mn=1.67
 (a=0.50, b=0.20, c=0.20, d=0.10)

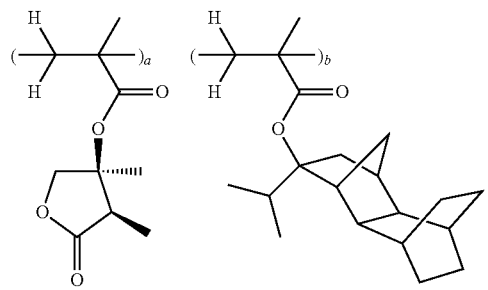

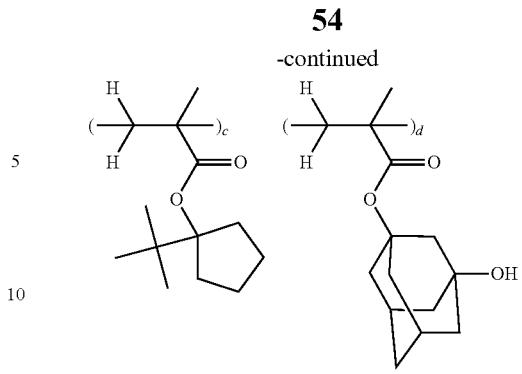

Polymer 2
 Mw=10,100
 Mw/Mn=1.70
 (a=0.50, b=0.40, c=0.10)

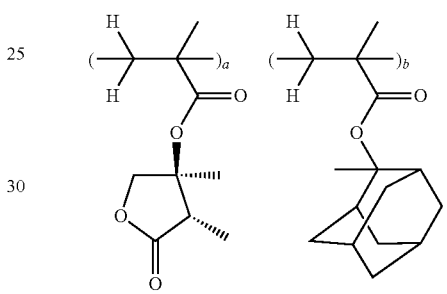

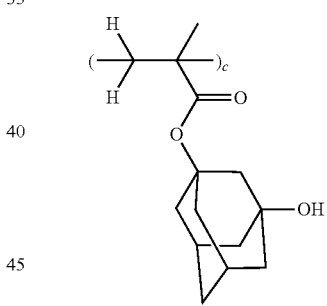

Polymer 3
 Mw=8,900
 Mw/Mn=1.72
 (a=0.50, b=0.20, c=0.20, d=0.10)

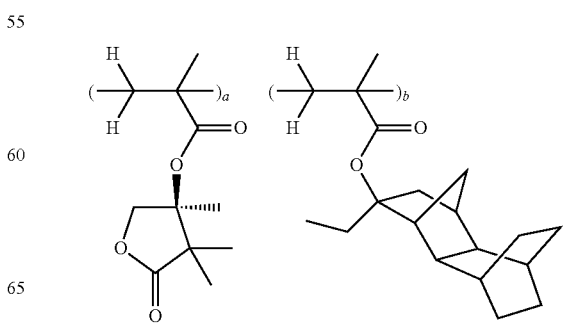

-continued
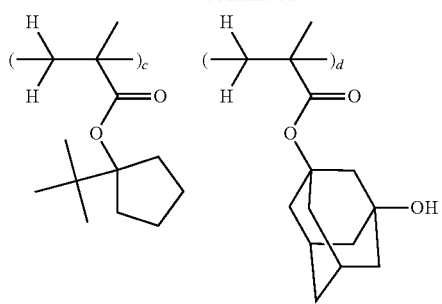
Polymer 4
 Mw=9,900
 Mw/Mn=1.66
 (a=0.30, b=0.50, c=0.20)
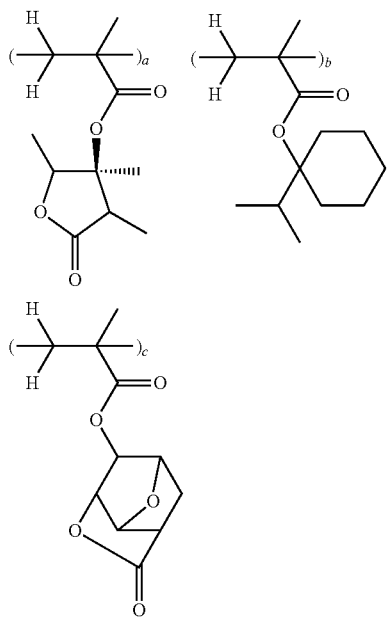
Polymer 5
 Mw=9,300
 Mw/Mn=1.55
 (a=0.30, b=0.40, c=0.10, d=0.20)
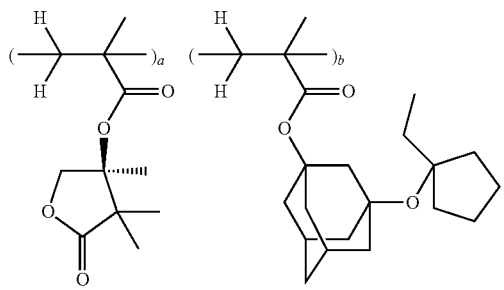
-continued
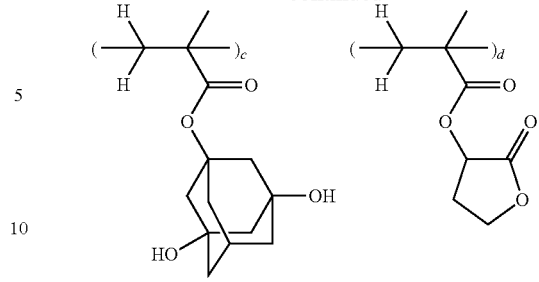
Polymer 6
 Mw=9,400
 Mw/Mn=1.57
 (a=0.35, b=0.30, c=0.20, d=0.15)
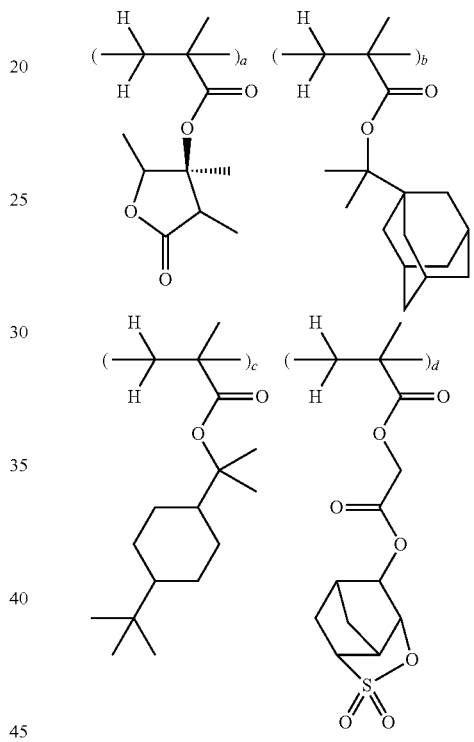
Polymer 7
 Mw=9,100
 Mw/Mn=1.67
 (a=0.35, b=0.35, c=0.15, d=0.15)
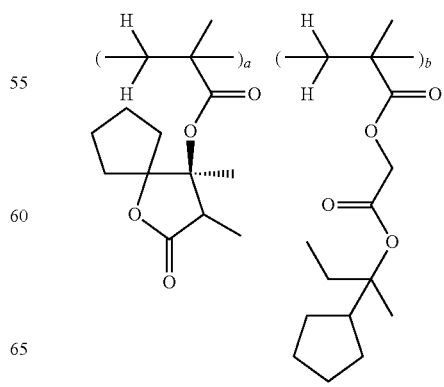

-continued
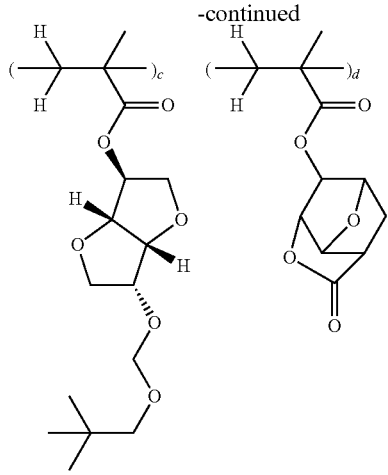
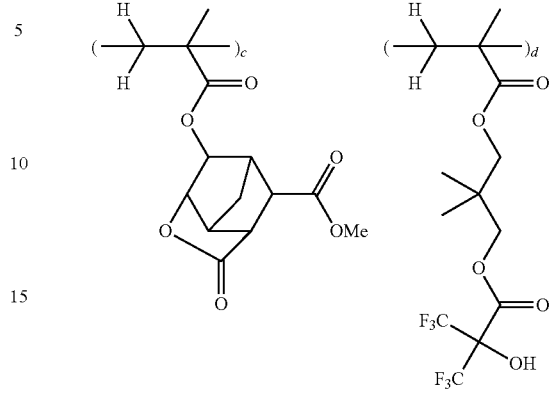
Polymer 8
Mw=7,900
Mw/Mn=1.73
(a=0.35, b=0.50, c=0.10, d=0.05)
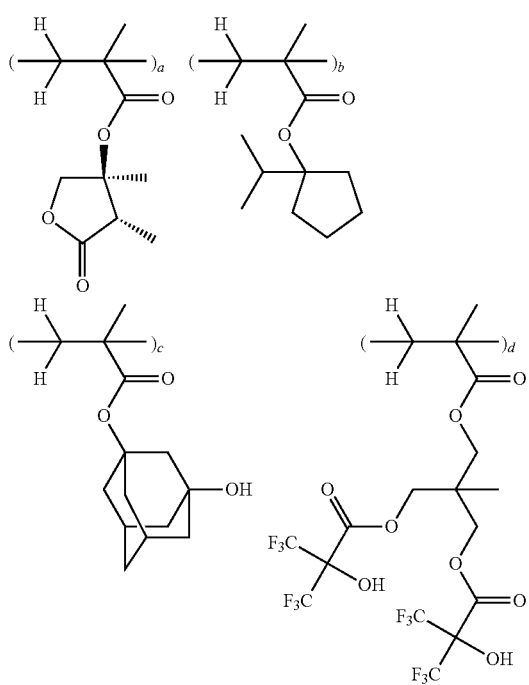
Polymer 9
Mw=8,500
Mw/Mn=1.63
(a=0.25, b=0.45, c=0.20, d=0.05, e=0.05)
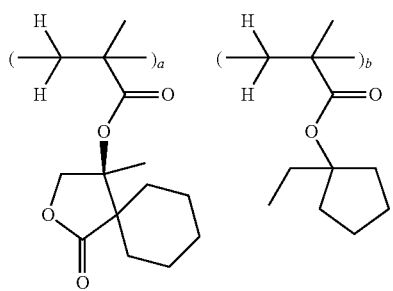
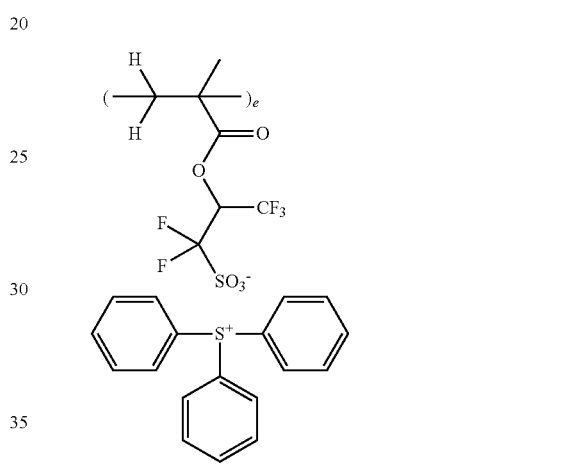
Polymer 10
Mw=8,800
Mw/Mn=1.54
(a=0.20, b=0.50, c=0.30)
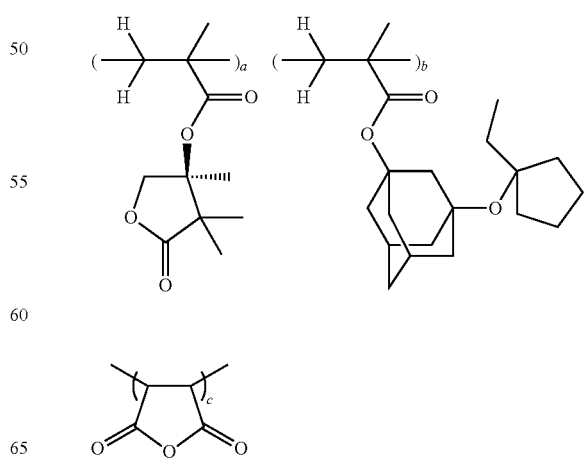

Polymer 11
  Mw=8,800
  Mw/Mn=1.61
  (a=0.55, b=0.35, c=0.10)
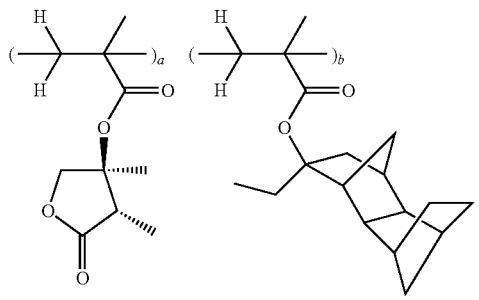
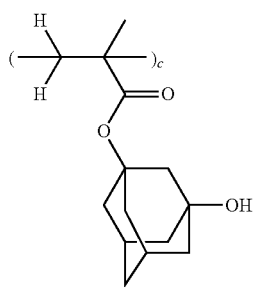
Polymer 12
  Mw=8,500
  Mw/Mn=1.52
  (a=0.55, b=0.35, c=0.10)
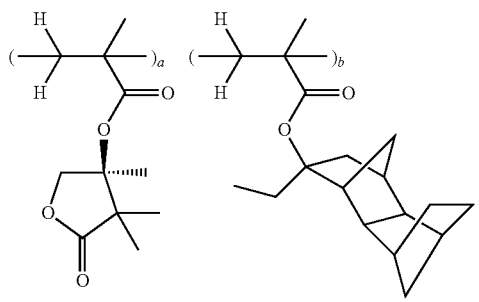
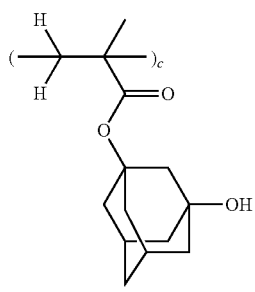
Polymer 13
  Mw=8,700
  Mw/Mn=1.59
  (a=0.55, b=0.35, c=0.10)
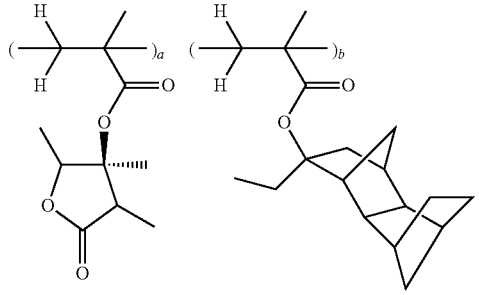
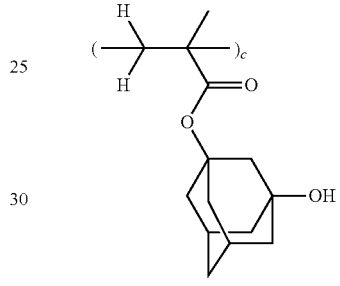
Comparative Polymer 1
  Mw=9,300
  Mw/Mn=1.53
  (a=0.50, b=0.20, c=0.20, d=0.10)
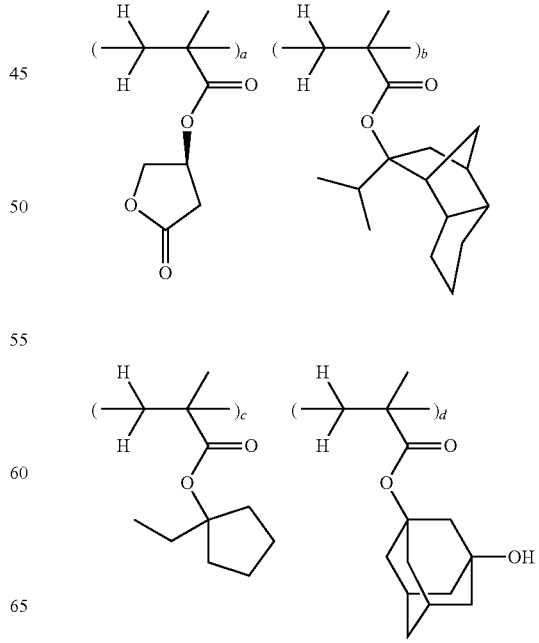

Comparative Polymer 2
 Mw=7,900
 Mw/Mn=1.60
 (a=0.45, b=0.25, c=0.20, d=0.10)
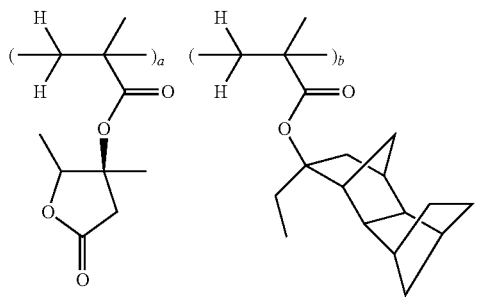
Comparative Polymer 3
 Mw=8,800
 Mw/Mn=1.66
 (a=0.30, b=0.30, c=0.20, d=0.20)
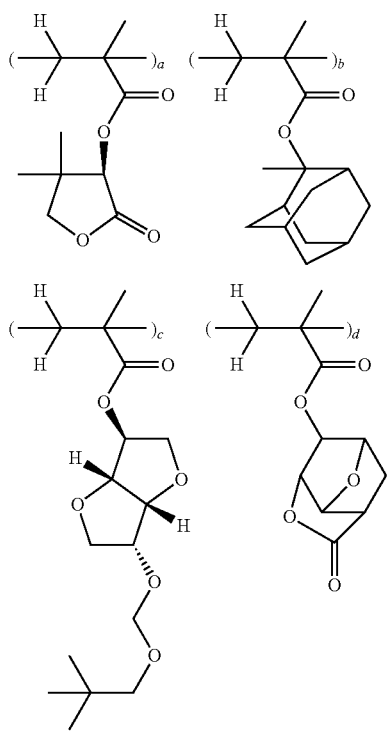
Comparative Polymer 4
 Mw=7,600
 Mw/Mn=1.59
 (a=0.40, b=0.50, c=0.10)
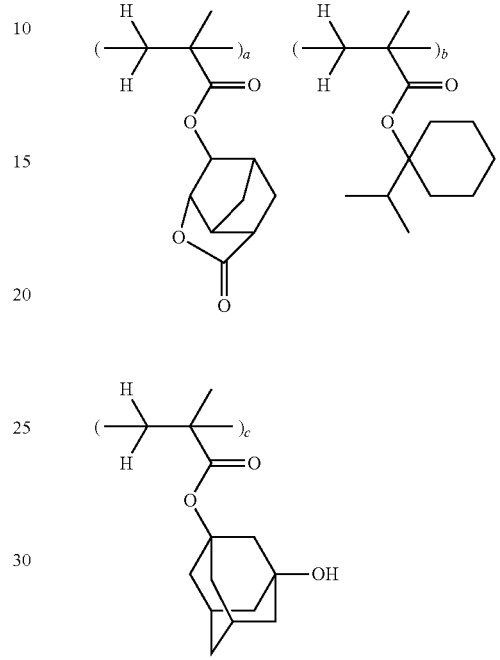
Comparative Polymer 5
 Mw=7,800
 Mw/Mn=1.54
 (a=0.55, b=0.35, c=0.10)
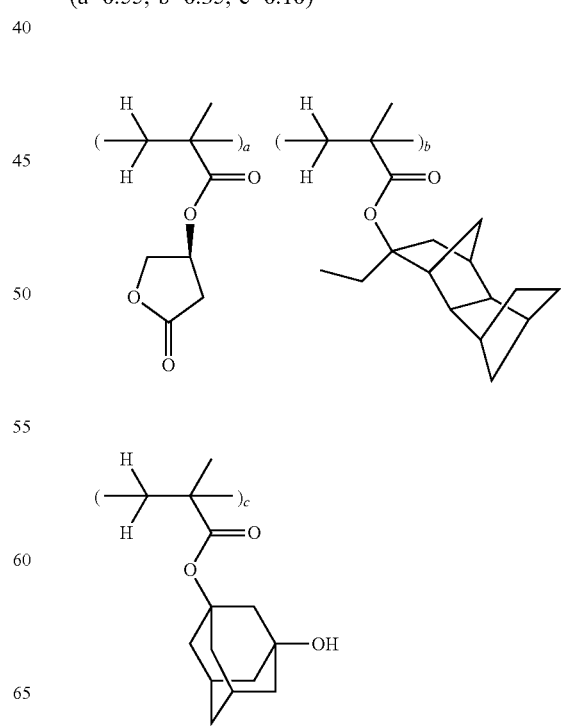

Comparative Polymer 6
Mw=8,000
Mw/Mn=1.57
(a=0.55, b=0.35, c=0.10)

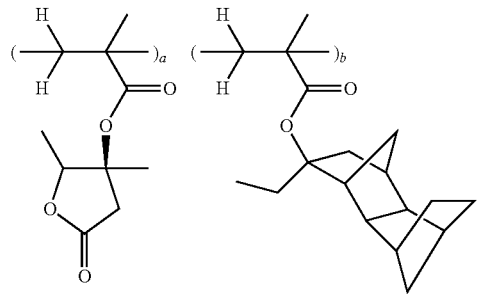

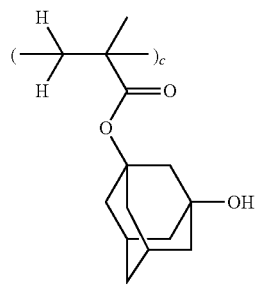

Reference Examples 1-1 to 1-13 and Comparative Examples 1-1 to 1-6

Preparation of Resist Composition

Resist compositions R-1 to R-19 in solution form were prepared by dissolving a polymer (Polymers 1 to 13 or Comparative Polymers 1 to 6) as base resin, photoacid generator, water-repellent polymer, and quencher in a solvent in accordance with the formulation of Tables 1 and 2 and filtering through a Teflon® filter with a pore size of 0.2 m. The photoacid generator (PAG-1 to 3), water-repellent polymer (SF-1, 2), quencher (Q-1 to 6), and solvent used herein are identified below.

Photoacid generator: PAG-1 to 3 shown below

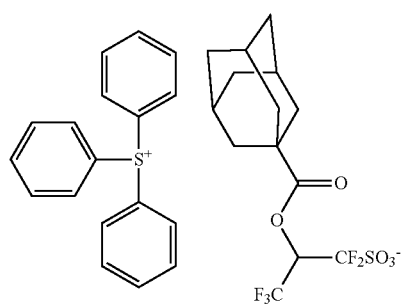

PAG-1

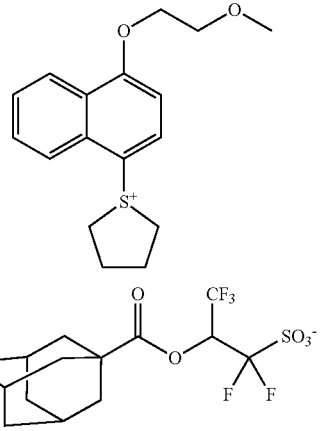

PAG-2

PAG-3

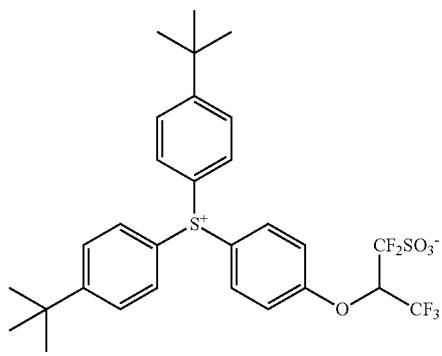

Water-repellent polymer: SF-1 and 2 shown below

SF-1

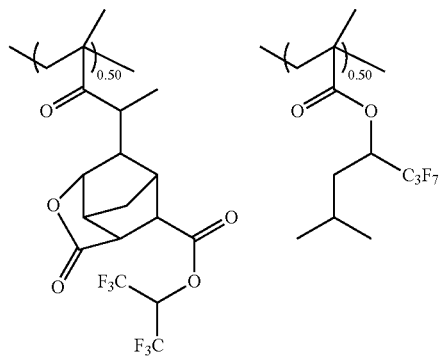

Mw = 7,500
Mw/Mn = 1.52

SF-2

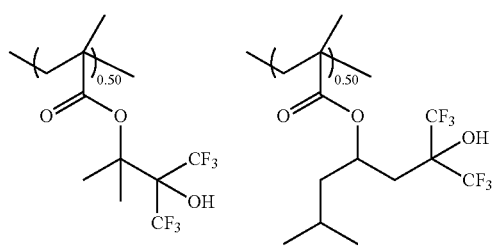

Mw = 8,800
Mw/Mn = 1.87

Quencher: Q-1 to 6 shown below

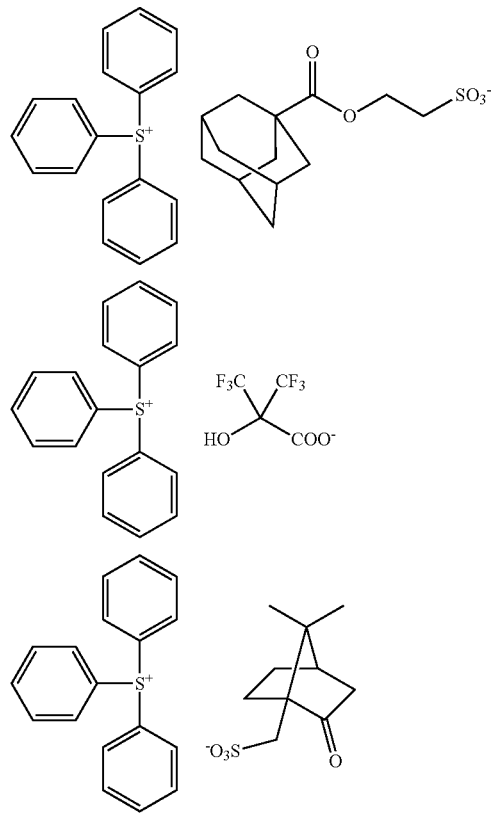

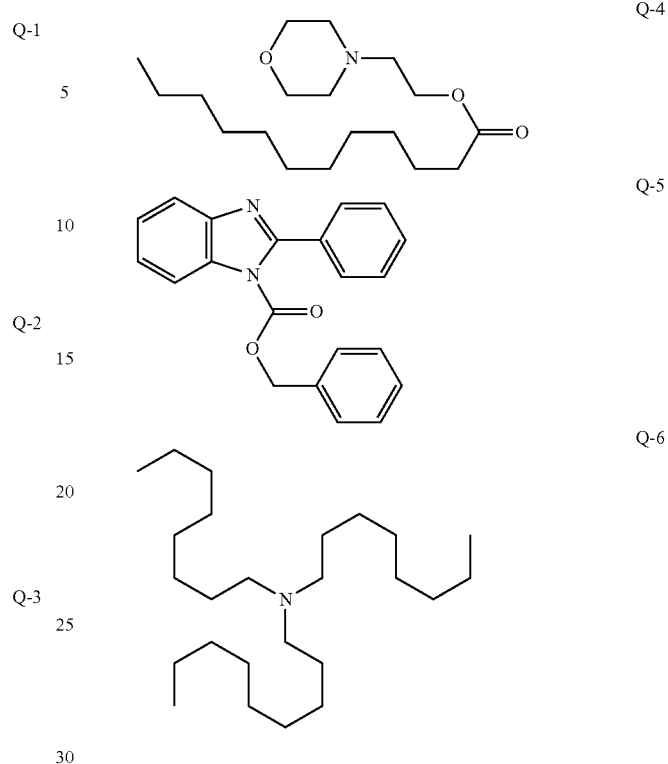

Organic solvent:

PGMEA (propylene glycol monomethyl ether acetate)

GBL (γ-butyrolactone)

PGME (propylene glycol monomethyl ether)

TABLE 1

|  |  | Resist | Resin (pbw) | PAG (pbw) | Quencher (pbw) | Water-repellent polymer (pbw) | Solvent (pbw) |
|---|---|---|---|---|---|---|---|
| Reference Example | 1-1 | R-1 | Polymer 1 (100) | PAG1 (10.0) | Q-1 (1.5) | SF-1 (6.0) | PGMEA(2,000) GBL(500) |
|  | 1-2 | R-2 | Polymer 2 (100) | PAG1 (10.0) | Q-2 (1.5) | SF-1 (6.0) | PGMEA(2,000) GBL(500) |
|  | 1-3 | R-3 | Polymer 3 (100) | PAG3 (8.0) | Q-2 (1.5) | SF-2 (6.0) | PGMEA(2,000) GBL(500) |
|  | 1-4 | R-4 | Polymer 4 (100) | PAG2 (12.5) | Q-1 (1.5) | SF-2 (6.0) | PGMEA(2,000) GBL(500) |
|  | 1-5 | R-5 | Polymer 5 (100) | PAG2 (12.5) | Q-2 (1.5) | SF-1 (6.0) | PGMEA(2,000) GBL(500) |
|  | 1-6 | R-6 | Polymer 6 (100) | PAG3 (8.0) | Q-1 (1.5) | SF-1 (6.0) | PGMEA(2,000) GBL(500) |
|  | 1-7 | R-7 | Polymer 7 (100) | PAG1 (10.0) | Q-3 (1.5) | SF-1 (6.0) | PGMEA(2,000) GBL(500) |
|  | 1-8 | R-8 | Polymer 8 (100) | PAG2 (12.5) | Q-1 (1.0) Q-4 (1.0) | — | PGMEA(2,000) GBL(500) |
|  | 1-9 | R-9 | Polymer 9 (100) | — | Q-3 (1.5) | — | PGMEA(500) GBL(1,450) PGME(50) |
|  | 1-10 | R-10 | Polymer 10 (100) | PAG1 (12.0) | Q-5 (1.5) | SF-2 (6.0) | PGMEA(2,000) GBL(500) |
|  | 1-11 | R-11 | Polymer 11 (100) | PAG1 (10.0) | Q-6 (1.5) | SF-1 (6.0) | PGMEA(2,000) GBL(500) |
|  | 1-12 | R-12 | Polymer 12 (100) | PAG1 (10.0) | Q-6 (1.5) | SF-1 (6.0) | PGMEA(2,000) GBL(500) |
|  | 1-13 | R-13 | Polymer 13 (100) | PAG1 (10.0) | Q-6 (1.5) | SF-1 (6.0) | PGMEA(2,000) GBL(500) |

TABLE 2

| | | Resist | Resin (pbw) | PAG (pbw) | Quencher (pbw) | Water-repellent polymer (pbw) | Solvent (pbw) |
|---|---|---|---|---|---|---|---|
| Comparative Example | 1-1 | R-14 | Comparative Polymer 1 (100) | PAG1 (10.0) | Q-1 (1.5) | SF-1 (6.0) | PGMEA(2,000) GBL(500) |
| | 1-2 | R-15 | Comparative Polymer 2 (100) | PAG1 (10.0) | Q-1 (1.5) | SF-1 (6.0) | PGMEA(2,000) GBL(500) |
| | 1-3 | R-16 | Comparative Polymer 3 (100) | PAG2 (12.5) | Q-2 (1.5) | SF-1 (6.0) | PGMEA(2,000) GBL(500) |
| | 1-4 | R-17 | Comparative Polymer 4 (100) | PAG3 (8.0) | Q-4 (1.0) | SF-1 (6.0) | PGMEA(2,000) GBL(500) |
| | 1-5 | R-18 | Comparative Polymer 5 (100) | PAG1 (10.0) | Q-6 (1.5) | SF-1 (6.0) | PGMEA(2,000) GBL(500) |
| | 1-6 | R-19 | Comparative Polymer 6 (100) | PAG1 (10.0) | Q-6 (1.5) | SF-1 (6.0) | PGMEA(2,000) GBL(500) |

Reference Examples 2-1 to 2-10 and Comparative Examples 2-1 to 2-4

ArF Lithography Patterning Test: Evaluation of L/S Pattern

On a substrate, a spin-on carbon film ODL-50 (Shin-Etsu Chemical Co., Ltd.) having a carbon content of 80 wt % was deposited to a thickness of 200 nm and a silicon-containing spin-on hard mask SHB-A940 having a silicon content of 43 wt % was deposited thereon to a thickness of 35 nm. On this substrate for trilayer process, the resist composition (R-1 to R-10) or comparative resist composition (R-14 to R-17) shown in Tables 1 and 2 was spin coated, then baked on a hot plate at 100° C. for 60 seconds to form a resist film of 100 nm thick. Using an ArF excimer laser immersion lithography scanner NSR-610C (Nikon Corp., NA 1.30, σ 0.98/0.78, 4/5 annular illumination), exposure was performed through Mask A. Mask A was a 6% halftone phase shift mask bearing a line pattern having a pitch of 100 nm and a line width of 50 nm (on-wafer size). After the exposure, the wafer was baked (PEB) at the temperature shown in Table 3 for 60 seconds and developed. Specifically, butyl acetate was injected from a development nozzle while the wafer was spun at 30 rpm for 3 seconds, which was followed by stationary puddle development for 27 seconds. The wafer was rinsed with 4-methyl-2-pentanol, spin dried, and baked at 100° C. for 20 seconds to evaporate off the rinse liquid. On solvent development, the unexposed region of resist film shielded by the mask was dissolved in the developer. This image reversal formed a line-and-space (L/S) pattern having a space width of 50 nm and a pitch of 100 nm.

Evaluation of Sensitivity

As an index of sensitivity, the optimum dose (Eop, mJ/cm$^2$) which provided an L/S pattern with a space width of 50 nm and a pitch of 100 nm was determined. A smaller dose value indicates a higher sensitivity.

Evaluation of Exposure Latitude (EL)

In L/S pattern formation through mask A, the exposure dose which provided an L/S pattern with a space width of 50 nm±10% (i.e., 45 nm to 55 nm) was determined. EL (%) is calculated from the exposure doses according to the following equation:

EL (%)=(|E1-E2|/Eop)×100 wherein E1 is an exposure dose which provides an L/S pattern with a space width of 45 nm and a pitch of 100 nm, E2 is an exposure dose which provides an L/S pattern with a space width of 55 nm and a pitch of 100 nm, and Eop is the optimum exposure dose which provides an L/S pattern with a space width of 50 nm and a pitch of 100 nm. A greater value of EL indicates better performance.

Evaluation of Line Width Roughness (LWR)

The L/S pattern formed by exposure in the optimum dose (determined in the sensitivity evaluation) was observed under TDSEM S-9380 (Hitachi Hitechnologies, Ltd.). The space width was measured at longitudinally spaced apart 10 points, from which a 3-fold value (3σ) of standard deviation (σ) was determined and reported as LWR. A smaller value of 3σ indicates a pattern having a lower roughness and more uniform space width.

The results are shown in Table 3.

TABLE 3

| | | Resist | PEB temp. (° C.) | Eop (mJ/cm$^2$) | EL (%) | LWR (nm) |
|---|---|---|---|---|---|---|
| Reference Example | 2-1 | R-1 | 85 | 25 | 17.4 | 3.4 |
| | 2-2 | R-2 | 100 | 29 | 19 | 3.1 |
| | 2-3 | R-3 | 95 | 26 | 18 | 3.2 |
| | 2-4 | R-4 | 90 | 28 | 16.5 | 3.2 |
| | 2-5 | R-5 | 105 | 29 | 18.5 | 3.3 |
| | 2-6 | R-6 | 95 | 27 | 15.9 | 3.4 |
| | 2-7 | R-7 | 95 | 25 | 18.3 | 3.4 |
| | 2-8 | R-8 | 85 | 26 | 16.6 | 3.4 |
| | 2-9 | R-9 | 90 | 28 | 18.2 | 3.3 |
| | 2-10 | R-10 | 90 | 26 | 20.5 | 3.4 |
| Comparative Example | 2-1 | R-14 | 85 | 31 | 13.2 | 4.5 |
| | 2-2 | R-15 | 85 | 28 | 8.3 | 5.1 |
| | 2-3 | R-16 | 90 | 33 | 11.5 | 4.4 |
| | 2-4 | R-17 | 90 | 38 | 12.1 | 5.8 |

Reference Examples 3-1 to 3-3 and Comparative Examples 3-1 to 3-2

ArF Lithography Test: Evaluation of Resist Storage Stability

The storage stability of the resist composition was examined by comparing the fresh Eop of a resist composition as freshly prepared and the aged Eop of the resist composition which was aged at 20° C. for 1 month. A percent sensitivity change (ΔS) is calculated according to the equation:

ΔS (%)=[(aged Eop−fresh Eop)]/(fresh Eop)×100

A negative value of ΔS indicates an increase of sensitivity during aging. A smaller magnitude of ΔS indicates that the resist composition experiences a less change during shelf storage, that is, higher storage stability.

The results are shown in Table 4.

TABLE 4

|  |  | Resist | Fresh Eop (mJ/cm$^2$) | ΔS (%) |
|---|---|---|---|---|
| Reference Example | 3-1 | R-11 | 38 | −1 |
|  | 3-2 | R-12 | 40 | 0 |
|  | 3-3 | R-13 | 43 | 0 |
| Comparative Example | 3-1 | R-18 | 39 | −9 |
|  | 3-2 | R-19 | 42 | −3 |

As is evident from Table 3, the resist compositions of Reference Examples are effective for forming negative patterns having improved LWR and EL via organic solvent development. As is evident from Table 4, the resist compositions of Reference Examples are fully shelf stable even when they contain a basic compound.

Japanese Patent Application No. 2014-097364 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:

1. A method for preparing a monomer having the general formula (1), comprising the steps of reacting a compound having the general formula (9) with a base or a metal selected from Group 1A, 2A and 2B metals to form a metal enolate reagent, and reacting the metal enolate reagent with an acyloxyketone compound having the general formula (8):

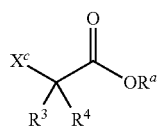
(9)

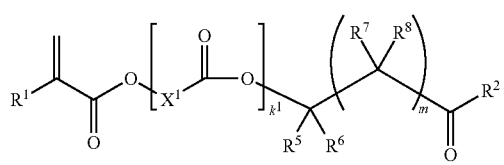
(8)

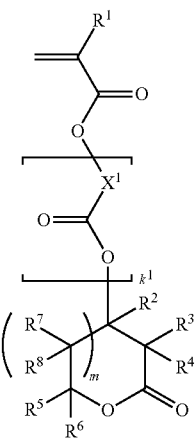
(1)

wherein R$^1$ is hydrogen, methyl or trifluoromethyl,
R$^2$ is hydrogen or a straight, branched or cyclic C$_1$-C$_{10}$ monovalent hydrocarbon group which may contain a heteroatom,
R$^3$ and R$^4$ are each independently hydrogen or a straight, branched or cyclic C$_1$-C$_{10}$ monovalent hydrocarbon group which may contain a heteroatom, R$^3$ and R$^4$ may bond together to form a ring with the carbon atom to which they are attached,
R$^5$ and R$^6$ are each independently hydrogen or a straight, branched or cyclic C$_1$-C$_{10}$ monovalent hydrocarbon group which may contain a heteroatom, R$^5$ and R$^6$ may bond together to form a ring with the carbon atom to which they are attached,
R$^7$ and R$^8$ are each independently hydrogen or a straight, branched or cyclic C$_1$-C$_{10}$ monovalent hydrocarbon group which may contain a heteroatom, R$^7$ and R$^8$ may bond together to form a ring with the carbon atom to which they are attached,
X$^1$ is a C$_1$-C$_{10}$ alkylene group which may have an ether, ester, lactone ring or hydroxyl, or a C$_6$-C$_{10}$ arylene group,
m is 0 or 1, in case of m=0, R$^2$ may bond with R$^5$ or R$^6$ to form a ring with the carbon atoms to which they are attached, in case of m=1, R$^2$ may bond with R$^7$ or R$^8$ to form a ring with the carbon atoms to which they are attached,
k$^1$ is 0 or 1,
X$^c$ is hydrogen or halogen, and
R$^a$ is a straight or branched C$_1$-C$_{10}$ monovalent hydrocarbon group.

2. A method for preparing a monomer having the general formula (1), comprising the steps of reacting a compound having the general formula (9) with a base or a metal selected from Group 1A, 2A and 2B metals to form a metal enolate reagent, reacting the metal enolate reagent with an acyloxyketone compound having the general formula (8), isolating the resulting intermediate having the general formula (12), and lactonizing the intermediate:

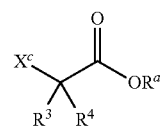
(9)

-continued (8)

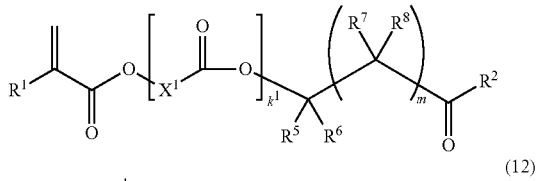

(12)

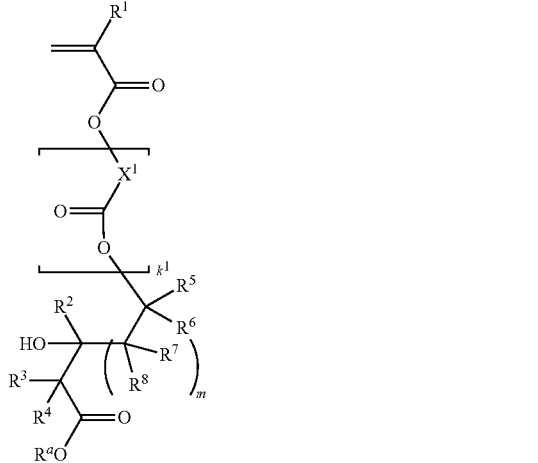

(1)

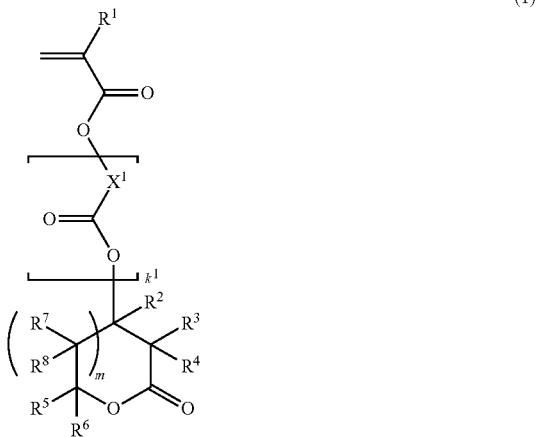

wherein $R^1$ is hydrogen, methyl or trifluoromethyl,
$R^2$ is hydrogen or a straight, branched or cyclic $C_1$-$C_{10}$ monovalent hydrocarbon group which may contain a heteroatom,
$R^3$ and $R^4$ are each independently hydrogen or a straight, branched or cyclic $C_1$-$C_{10}$ monovalent hydrocarbon group which may contain a heteroatom, $R^3$ and $R^4$ may bond together to form a ring with the carbon atom to which they are attached,
$R^5$ and $R^6$ are each independently hydrogen or a straight, branched or cyclic $C_1$-$C_{10}$ monovalent hydrocarbon group which may contain a heteroatom, $R^5$ and $R^6$ may bond together to form a ring with the carbon atom to which they are attached,
$R^7$ and $R^8$ are each independently hydrogen or a straight, branched or cyclic $C_1$-$C_{10}$ monovalent hydrocarbon group which may contain a heteroatom, $R^7$ and $R^8$ may bond together to form a ring with the carbon atom to which they are attached,
$X^1$ is a $C_1$-$C_{10}$ alkylene group which may have an ether, ester, lactone ring or hydroxyl, or a $C_6$-$C_{10}$ arylene group,
m is 0 or 1, in case of m=0, $R^2$ may bond with $R^5$ or $R^6$ to form a ring with the carbon atoms to which they are attached, in case of m=1, $R^2$ may bond with $R^7$ or $R^8$ to form a ring with the carbon atoms to which they are attached,
$k^1$ is 0 or 1,
$X^c$ is hydrogen or halogen, and
$R^a$ is a straight or branched $C_1$-$C_{10}$ monovalent hydrocarbon group.

3. The method of claim 1 wherein the acyloxyketone compound having formula (8) is prepared by reaction of a haloketone compound having the general formula (4) with a carboxylic acid salt compound having the general formula (5):

(4)

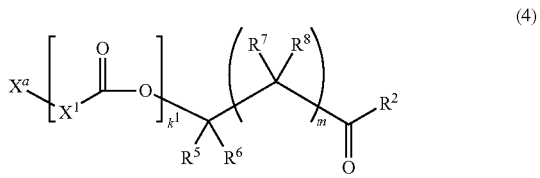

(5)

wherein $R^1$, $R^2$, $R^5$, $R^6$, $R^7$, $R^8$, $X^1$, m and $k^1$ are as defined above, $X^a$ is halogen, and $M^a$ is Li, Na, K, $Mg_{1/2}$, $Ca_{1/2}$ or substituted or unsubstituted ammonium.

4. The method of claim 1 wherein the acyloxyketone compound having formula (8) is prepared by reaction of an alcohol compound having the general formula (6) with an esterifying agent having the general formula (7):

(6)

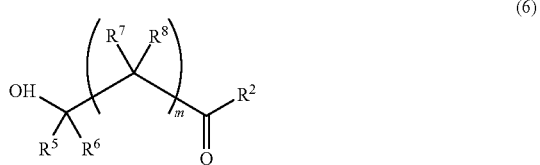

(7)

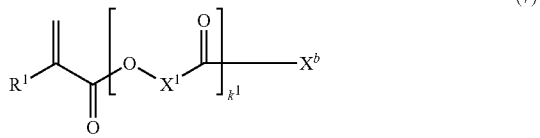

wherein $R^1$, $R^2$, $R^5$, $R^6$, $R^7$, $R^8$, $X^1$, m and $k^1$ are as defined above, $X^b$ is halogen, hydroxyl or —$OR^b$, and $R^b$ is methyl, ethyl or a group having the formula (11):

(11)

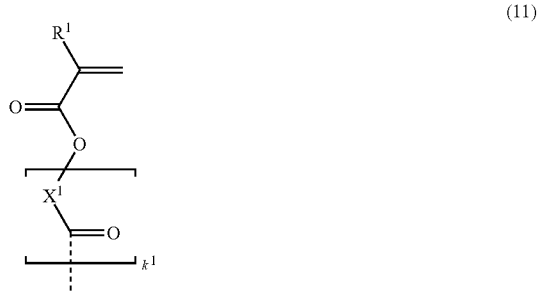

wherein $R^1$, $X^1$ and $k^1$ are as defined above, and the broken line denotes a valence bond.

* * * * *